US008986212B2

(12) United States Patent
Hyoun et al.

(10) Patent No.: US 8,986,212 B2
(45) Date of Patent: Mar. 24, 2015

(54) ULTRASONIC DIAGNOSTIC APPARATUS

(75) Inventors: Dong Gyu Hyoun, Gwangju-si (KR); Jong Sik Kim, Gwangjin-gu (KR)

(73) Assignee: Samsung Medison Co., Ltd., Hongchun-Gun, Kangwon-Do (KR)

( * ) Notice: Subject to any disclaimer, the term of this patent is extended or adjusted under 35 U.S.C. 154(b) by 406 days.

(21) Appl. No.: 13/107,437

(22) Filed: May 13, 2011

(65) Prior Publication Data

US 2011/0282212 A1 Nov. 17, 2011

(30) Foreign Application Priority Data

May 14, 2010 (KR) ........................ 10-2010-0045272
May 14, 2010 (KR) ........................ 10-2010-0045273
May 14, 2010 (KR) ........................ 10-2010-0045274
May 14, 2010 (KR) ........................ 10-2010-0045275

(51) Int. Cl.
*A61B 8/00* (2006.01)

(52) U.S. Cl.
CPC ................ *A61B 8/00* (2013.01); *A61B 8/4227* (2013.01); *A61B 8/4461* (2013.01); *A61B 8/4472* (2013.01)
USPC ........... 600/459; 600/437; 600/441; 600/443; 601/2; 601/3; 601/4

(58) Field of Classification Search
USPC ........................... 600/407, 437–475; 601/2–4
See application file for complete search history.

(56) References Cited

U.S. PATENT DOCUMENTS 4,681,120 A 7/1987 Kunii
6,110,111 A 8/2000 Barnard
2007/0038112 A1 2/2007 Taylor et al.
2008/0262347 A1 10/2008 Batchelder et al.
2009/0036780 A1 2/2009 Abraham

FOREIGN PATENT DOCUMENTS

WO WO 2006/121765 A2 11/2006
WO WO 2006/131881 A1 12/2006
WO WO 2007/057826 A1 5/2007
WO WO 2007/069157 A2 6/2007
WO WO 2007/120873 A2 10/2007
WO WO 2007/130526 A2 11/2007
WO WO 2008/048708 A2 4/2008

OTHER PUBLICATIONS

Extended European Search Report issued in European Patent Application No. 11161834.4, dated Sep. 7, 2011.

*Primary Examiner* — Mark Remaly
(74) *Attorney, Agent, or Firm* — McDermott Will & Emery LLP

(57) ABSTRACT

The present disclosure provides an ultrasonic diagnostic apparatus. The ultrasonic diagnostic apparatus includes a fastening part having a band shape and wound around a diagnosis object, and a mover moving a probe along the fastening part.

13 Claims, 32 Drawing Sheets

1
22
26
90
14
42
30
46
40
20
70
92
72
24
44
29

3
21
92
40
46
42
80
22
14
72
30
44
26
90
48

3
92
80
46
42
22
44
14
30
21
26
90
48
80

190
10
120
180
182
12
137
100
130
136
140
138
184
146

401
450
452
420
433
430
436
442
440
435
446
432
425
480
434
437
438
439

401
450
452
433
430
420
436
442
440
435
446
432
425
480
434
437
438
439

464
446
435
425
462
402
460
420
433
434
430
436
442
440

402
430
433
420
435
432
446
436
464
442
440
439
438
437
434
460
462

402
430
433
420
435
432
446
434
460
462
436
464
442
440
439
438
437

ULTRASONIC DIAGNOSTIC APPARATUS

BACKGROUND

1. Technical Field

The present disclosure relates to an ultrasonic diagnostic apparatus and, more particularly, to an ultrasonic diagnostic apparatus which allows a probe to move along a diagnosis object having a rounded surface or protruded portion so as to facilitate ultrasonic diagnosis on the rounded surface or protuberances of the object.

2. Description of the Related Art

Generally, an ultrasonic diagnostic apparatus refers to a non-invasive apparatus that irradiates an ultrasound signal from a surface of a patient body towards a target internal organ beneath the body surface and obtains an image of a monolayer or blood flow in soft tissue from information in the reflected ultrasound signal (ultrasound echo-signal).

The ultrasonic diagnostic apparatus has been widely used for diagnosis of the heart, the abdomen, the urinary organs, and in obstetrics and gynecology due to various merits thereof such as small size, low price, real-time image display, and high stability through elimination of radiation exposure, as compared with other image diagnostic systems, such as X-ray diagnostic systems, computerized tomography scanners (CT scanners), magnetic resonance imagers (MRIs), nuclear medicine diagnostic apparatuses, and the like.

The ultrasonic diagnostic apparatus includes a probe which transmits an ultrasound signal to a diagnosis object and receives the ultrasound signal reflected therefrom to obtain ultrasound images of the diagnosis object. A controller displays the signal sent from the probe on a display screen, so that a user can diagnose the object while alternately viewing the screen and the object.

Meanwhile, a diagnosis of thyroid cancer or hyperthyroidism must be verified through ultrasound examination of the neck region. Ultrasound scanning for thyroid examination is conducted using a probe around the neck of a patient laid on an examination table. Here, it should be noted that the above description is provided for understanding of the background art and is not a description of a well-known conventional technique to which the present disclosure pertains.

In ultrasonic diagnosis for thyroid examination, since the neck has a rounded circumference and protuberances, a user of the ultrasonic diagnostic apparatus grips and moves the probe along the neck to scan the thyroid. Such manipulation of the probe for thyroid examination can provide non-uniform ultrasound images depending on user's skill, thereby lowering reliability of the ultrasonic diagnosis. Moreover, since a user must move the probe along a rounded surface or protuberances of the neck, the user may experience wrist strain or the like. Therefore, there is a need for an improved ultrasonic diagnostic apparatus.

BRIEF SUMMARY

The present disclosure is directed to solving such problems of the related art, and an aspect of the present disclosure is to provide an ultrasonic diagnostic apparatus which guarantees reliability in ultrasonic diagnosis of an object including the neck regardless of user's skill.

Another aspect of the present disclosure is to provide an ultrasonic diagnostic apparatus which may reduce user fatigue.

A further aspect of the present disclosure is to provide an ultrasonic diagnostic apparatus which allows a probe to be brought into close contact with a diagnosis object so as not to form a gap between the probe and the diagnosis object during diagnosis.

Yet another aspect of the present disclosure is to provide an ultrasonic diagnostic apparatus which can prevent significant acoustic reflection or multiple reflection by repeated reflection on a contact surface between the probe and a body surface such as the skin due to a large difference in acoustic impedance therebetween when the probe is brought into direct contact with the body surface, thereby solving the problem of deterioration in quality of ultrasound images resulting from poor transmission of acoustic signals through the skin during diagnosis.

Yet another aspect of the present disclosure is to provide an ultrasonic diagnostic apparatus which can solve the problem of deterioration in quality of ultrasound images due to a Fresnel Zone created near the probe and having a complex ultrasonic field due to non-uniform acoustic signal intensity, when the probe is brought into direct contact with the body surface.

In accordance with one aspect, an ultrasonic diagnostic apparatus includes: a fastening part having a band shape and wound around a diagnosis object; and a mover moving a probe along the fastening part.

The fastening part may include an ultrasound permeable film connected to the mover and a band member connected to the ultrasound permeable film.

The band member may include a first band member connected to one side of the ultrasound permeable film and a second band member connected to the other side of the ultrasound permeable film.

The apparatus may further include a fluid supply part connected to the first and second band members to supply hydraulic pressure. The first and second band members are expanded by the hydraulic pressure.

The apparatus may further include a gel pad having a gel therein and disposed on one side of the ultrasound permeable film facing the diagnosis object.

The fastening part may include a resilient gel pad disposed in a moving direction of the mover to surround the mover, and a band member connected to the gel pad.

The probe may be moved in a state of contacting an outer surface of the gel pad when probing the diagnosis object.

The probe may be disposed within the gel pad.

The mover may include a drive member supplying rotational power, a conveyor belt moved by rotation of the drive member, and a movable mounting part moved in conjunction with the conveyor belt and having the probe secured to one side thereof.

The mover may include a gear rack disposed on the fastening part in a longitudinal direction in which the probe is moved, and a movable examination part moving along the gear rack and having the probe secured to a side surface thereof.

The movable examination part may include a pinion member engaging with the gear rack, a transport motor driving the pinion member, and a movable plate on which the transport motor, pinion member and probe are mounted.

The mover may include a first mover moving the probe in a first direction along the fastening part and a second mover moving the probe in a second direction different from the first direction along the fastening part.

The first mover may include a first drive member supplying rotational power, a conveyor belt moved by rotation of the first drive member, and a movable mounting part moved in conjunction with the conveyor belt and having the probe secured to one side thereof. The second mover may include a guide rail formed in the second direction and having first teeth formed on a side surface of the guide rail, a movable bracket moving along the guide rail, a rotational gear formed on the movable bracket and having second teeth engaging with the first teeth, and a second drive member rotating the rotational gear.

The mover may further include a rotator rotating the probe.

The rotator may include a rotational motor supplying rotational power and a rotational bracket connected to an output shaft of the rotational motor while surrounding a side surface of the probe.

BRIEF DESCRIPTION OF THE DRAWINGS

The above and other aspects, features and advantages of the present disclosure will become apparent from the following description of the following embodiments given in conjunction with the accompanying drawings, in which.

DETAILED DESCRIPTION

Figure 1:
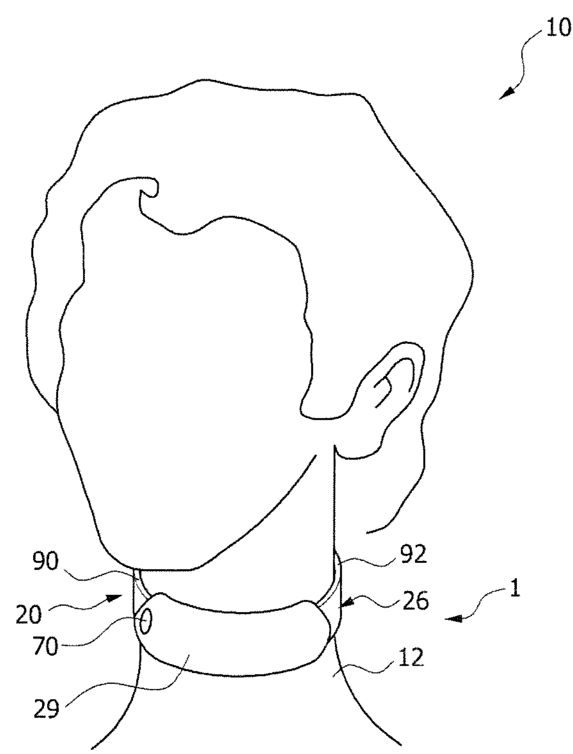
FIG. 1 is a perspective view of an ultrasonic diagnostic apparatus according to a first embodiment of the present disclosure in use.
Figure 2:
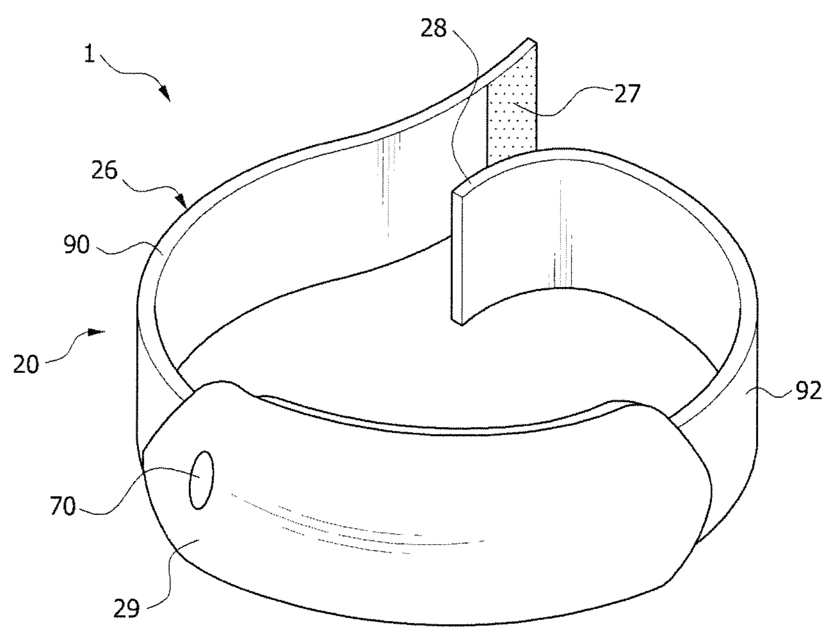
FIG. 2 is a perspective view of the ultrasonic diagnostic apparatus according to the first embodiment of the present disclosure.
Figure 3:
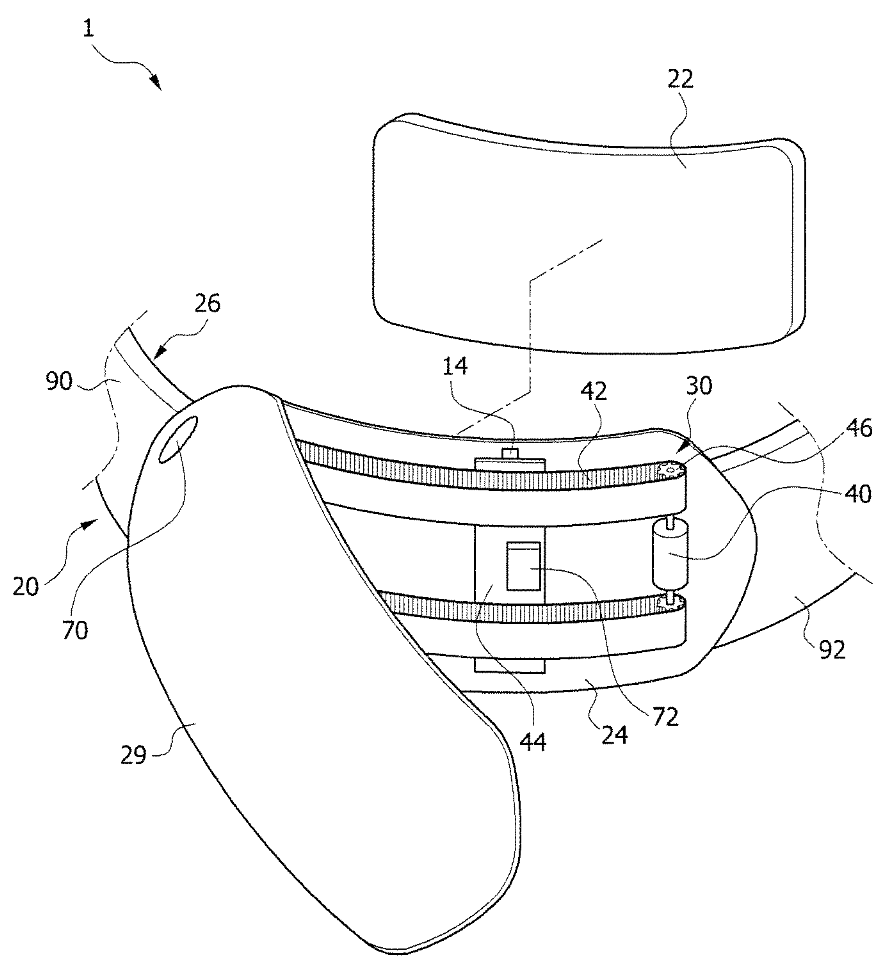
FIG. 3 is an exploded perspective view of the ultrasonic diagnostic apparatus according to the first embodiment of the present disclosure.

Embodiments of the present disclosure will now be described in detail with reference to the accompanying drawings. In descriptions of the following embodiments, an ultrasonic diagnostic apparatus for thyroid examination will be described by way of example. It should be noted that the drawings are not to precise scale and may be exaggerated in thickness of lines or size of components for descriptive convenience and clarity. Furthermore, terms used herein are defined by taking functions of the present disclosure into account and can be changed according to the custom or intention of users or operators. Therefore, definition of the terms should be made according to overall disclosures set forth herein.

FIGS. 1 to 6 show an ultrasonic diagnostic apparatus according to a first embodiment of the present disclosure.

Referring to FIGS. 1 to 6, an ultrasonic diagnostic apparatus 1 according to the first embodiment includes a fastening part 20 that has a band shape and is wound around a diagnosis object 10, and a mover 30 that moves a probe 14 for transmitting and receiving ultrasound signals along the fastening part 20.

In the first embodiment, the diagnosis object 10 is a person and the ultrasonic diagnostic apparatus 1 is wound around the neck 12 of the person for thyroid examination.

The fastening part 20 is wound around the neck 12, and the probe 14 is used to perform ultrasound examination of the thyroid while moving along the circumference of the neck 12.

Any device may serve as the probe 14 for the ultrasonic diagnostic apparatus 1 so long as the device can obtain ultrasound images of the diagnosis object 10 while transmitting or receiving ultrasound signals.

The fastening part 20 is wound around the diagnosis object 10 such as the neck 12 of a person and the mover 30 is disposed on a side surface of or inside the fastening part 20 to move the probe 14 automatically.

Any stretchable member such as a string or band may serve as the fastening part 20 so long as the member allows the mover 30 to be positioned at any suitable location facilitating acquisition of ultrasound imagery of the diagnosis object 10.

In the first embodiment, the fastening part 20 includes an ultrasound permeable film 24 connected to the mover 30 and a band member 26 connected to the ultrasound permeable film 24.

The ultrasound permeable film 24 may be made of any stretchable material that has high permeability to ultrasound waves and can be wrapped around the neck 12.

A gel pad 22 may be disposed to adjoin the ultrasound permeable film 24. Obviously, the ultrasonic diagnostic apparatus 1 may use the ultrasound permeable film 24 without the gel pad 22.

The gel pad 22 is provided to one side of the ultrasound permeable film 22 facing the diagnosis object 10 and includes an ultrasound permeable gel therein.

When the probe 14 is used to examine the neck 12, the gel pad 22 is in close contact with the neck 12 along the circumference thereof, thereby preventing measurement errors caused by the formation of a gap between the probe 14 and the diagnosis object 10.

The band member 26 includes a first band member 90 connected to one side of the ultrasound permeable film 24 and a second band member 92 connected to the other side of the ultrasound permeable film 24.

The band member 26 may further include a first fastener 27 connected to the first band member 90 and a second fastener 28 connected to the second band member 92 to be fastened to the first fastener 27. Any members may be employed as the first and second fasteners 27, 28 so long as the members can be fastened to each other.

In this embodiment, fabric hook-and-loop fasteners such as Velcro fasteners are provided as the first and second fasteners 27, 28, thereby allowing easy adjustment in length and easy attachment/detachment of the band member 26 to the object 10.

Figure 4:
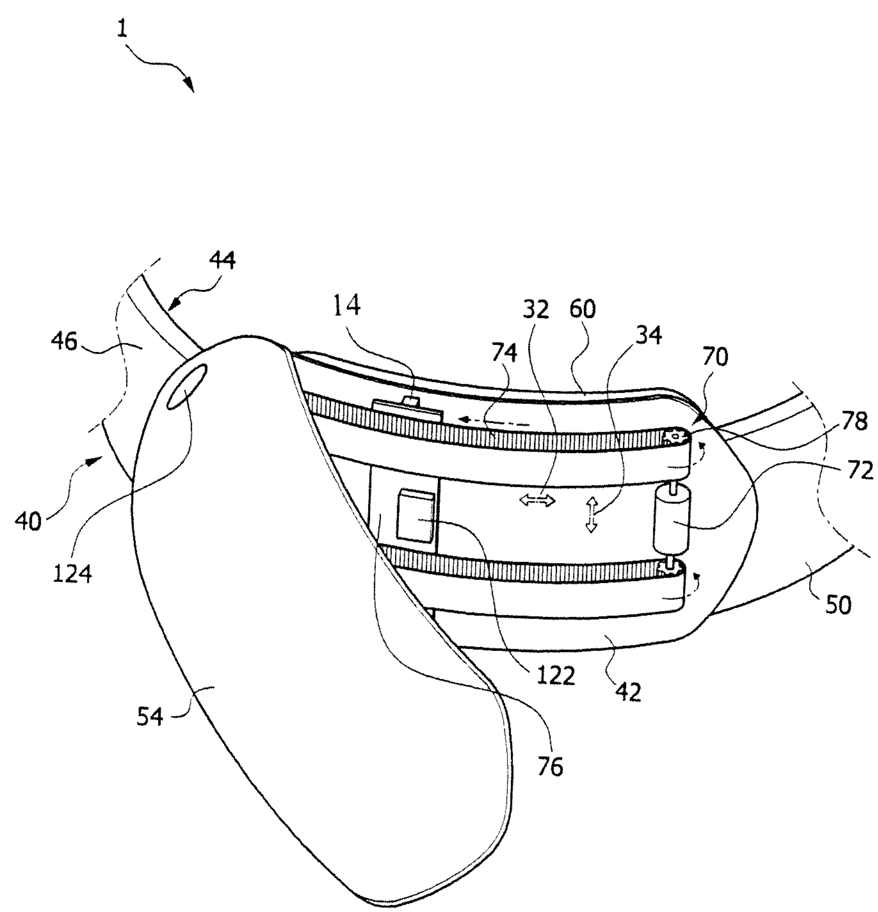
FIG. 4 is a perspective view of the ultrasonic diagnostic apparatus according to the first embodiment of the present disclosure, showing a movable mounting part that moves on conveyor belts in FIG. 3.

Any device may be employed as the mover 30 of the ultrasound permeable film 24 so long as the device can move the probe 14 in a longitudinal direction (in FIG. 4).

In the first embodiment, the mover 30 includes a drive member 40 for supplying rotational power, conveyor belts 42 moved by rotation of the drive member 40, a movable mounting part 44 moved in conjunction with the conveyor belts 42 and having the probe 14 secured to one side thereof, a drive gear 46 powered by the drive member 40 and supporting one side of each of the conveyor belts 42, and a driven gear 48 supporting the other side of each of the conveyor belts 44.

The drive member 40 includes a motor for supplying rotational power and is secured to the ultrasound permeable film 24.

Figure 5:
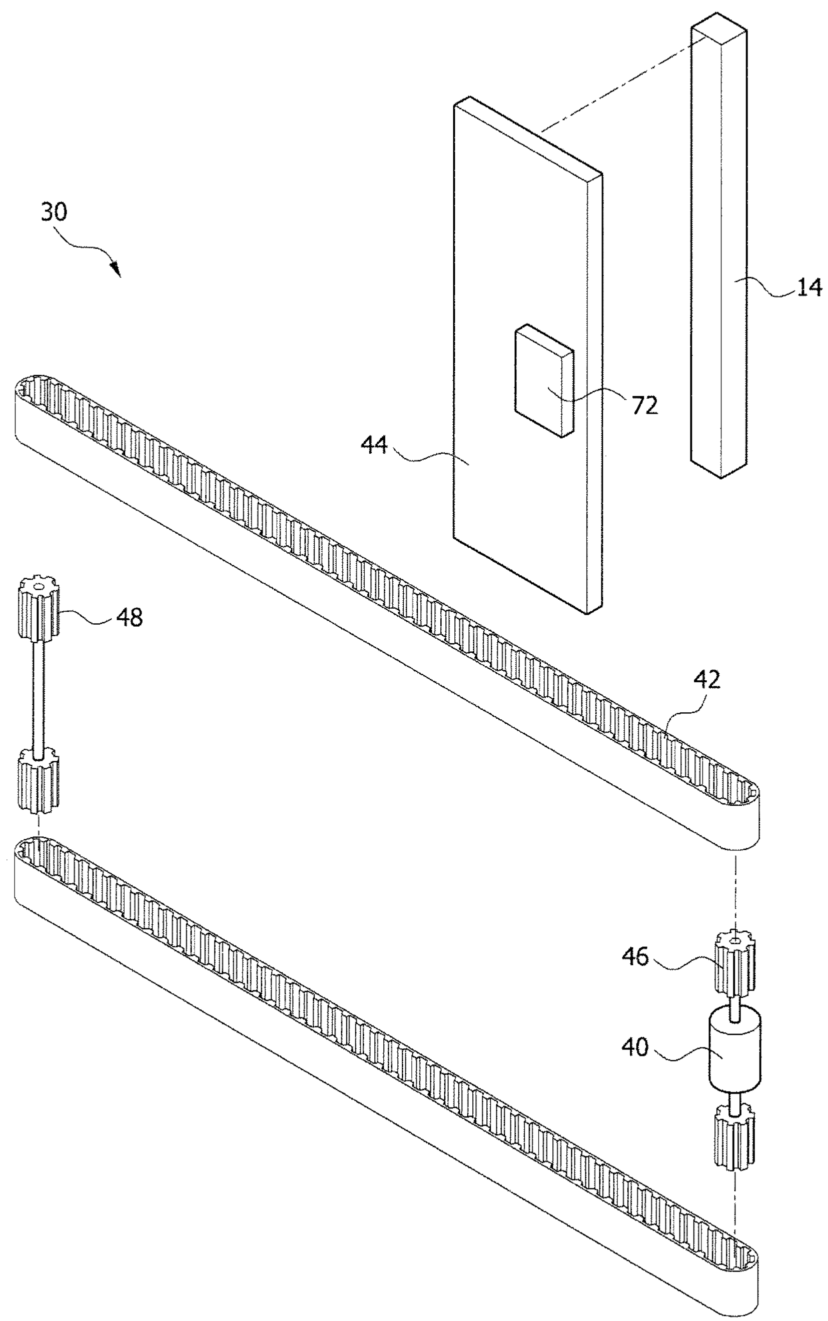
FIG. 5 is an exploded perspective view of a mover of the ultrasonic diagnostic apparatus according to the first embodiment of the present disclosure.
Figure 6:
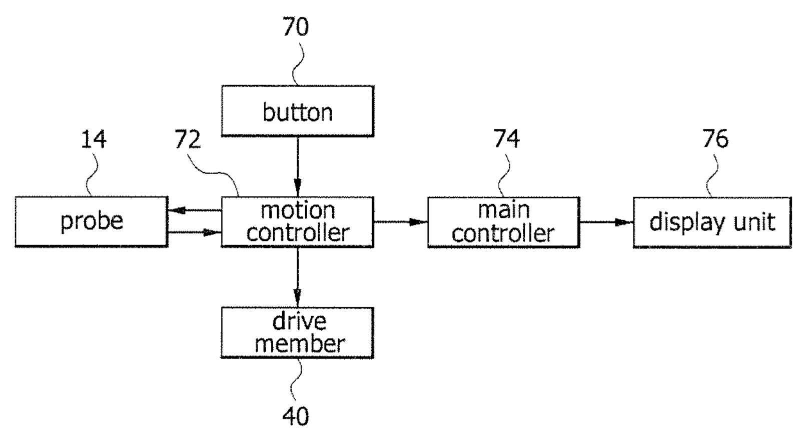
FIG. 6 is a block diagram of the ultrasonic diagnostic apparatus according to the first embodiment of the present disclosure.

The drive gear 46 is coupled to either side of a shaft extending through the drive member 40 in a vertical direction (in FIG. 5).

The drive gear 46 supports the one side (right side in FIG. 5) of each conveyor belt 42 and the driven gear 48 supports the other side of each conveyor belt 42.

The driven gear 48 is also coupled to either side of a connection bar, which connects both driven gears 45 such that the driven gears 45 are simultaneously rotated.

The conveyor belt 42 has a threaded inner surface, which engages with the drive gear 46 and driven gear 48 to rotate therewith.

With the probe 14 mounted on the movable mounting part 44, the movable mounting part 44 is secured to the conveyor belts 42 and moved in conjunction with the conveyor belts 42.

Since the conveyor belts 42 are disposed at opposite sides of the movable mounting part 44, the movable mounting part 44 may be more stably moved in the longitudinal direction of the conveyor belts 42 (in FIG. 5).

The movable mounting part 44 is provided with a motion controller 72 which controls operation of the drive member 40 and probe 14.

The motion controller 72 is controlled by a button 70, which may be disposed on a cover 29 covering the ultrasound permeable film 24.

The motion controller 72 is connected to a main controller 74 via wired or wireless communication to send an ultrasound signal of the probe 14 thereto, and the main controller 74 converts the ultrasound signal into an image signal and sends the image signal to a display unit 76.

The mover 30 is operated by manipulation of the button 70 on the cover 26 and the drive member 40 is powered via wired or wireless communication or by a separate battery in the fastening part 20.

Next, operation of the ultrasonic diagnostic apparatus according to the first embodiment will be described with reference to the accompanying drawings.

With the fastening part 20 wound around the neck 12 of a diagnosis object 10, the first fastener 27 is fastened to the second fastener 28 to secure the fastening part 20 to the neck 12.

With the fastening part 20 secured to the neck 12, the mover 30 including the probe 14 is placed in front of the neck 12 where the thyroid is located (at the left side in FIG. 1).

When a user presses the button 70, power is supplied to the drive member 40 to generate rotational power, which is transmitted to and rotates the drive gears 46 located at the opposite sides of the drive member 40.

Rotation of the drive gears 46 leads to rotation of the conveyor belts 42 between the drive gears 46 and the driven gears 48.

The movable mounting part 44 secured to the conveyor belts 42 is also moved together with the conveyor belts 42 and the probe 14 mounted on the movable mounting part 44 is also moved while scanning the thyroid to generate thyroid ultrasound imagery.

Since the gel pad 22 attached to the rear of the ultrasound permeable film 24 is disposed to surround the neck 12 having a curved shape, it is possible to reduce measurement errors that can occur due to the formation of pockets of air between the probe 14 and the diagnosis object 10 during ultrasonic diagnosis.

The motion controller 72 calculates a current location of the probe 14 and adjusts rotation of the drive member 40 in a forward or rearward direction to move the probe 14 in the longitudinal direction (in FIG. 4).

Then, an ultrasound signal is transmitted from the probe 14 to the main controller 74 via the motion controller 72. Then, the main controller 62 converts the ultrasound signal into an image signal and sends the image signal to a display unit 66, thereby providing thyroid ultrasound imagery.

Next, an ultrasonic diagnostic apparatus 2 according to a second embodiment will be described with reference to the accompanying drawings.

For convenience of description, the same elements as those of the first embodiment will be denoted by the same reference numerals and elaboration thereof will be omitted herein.

Figure 7:
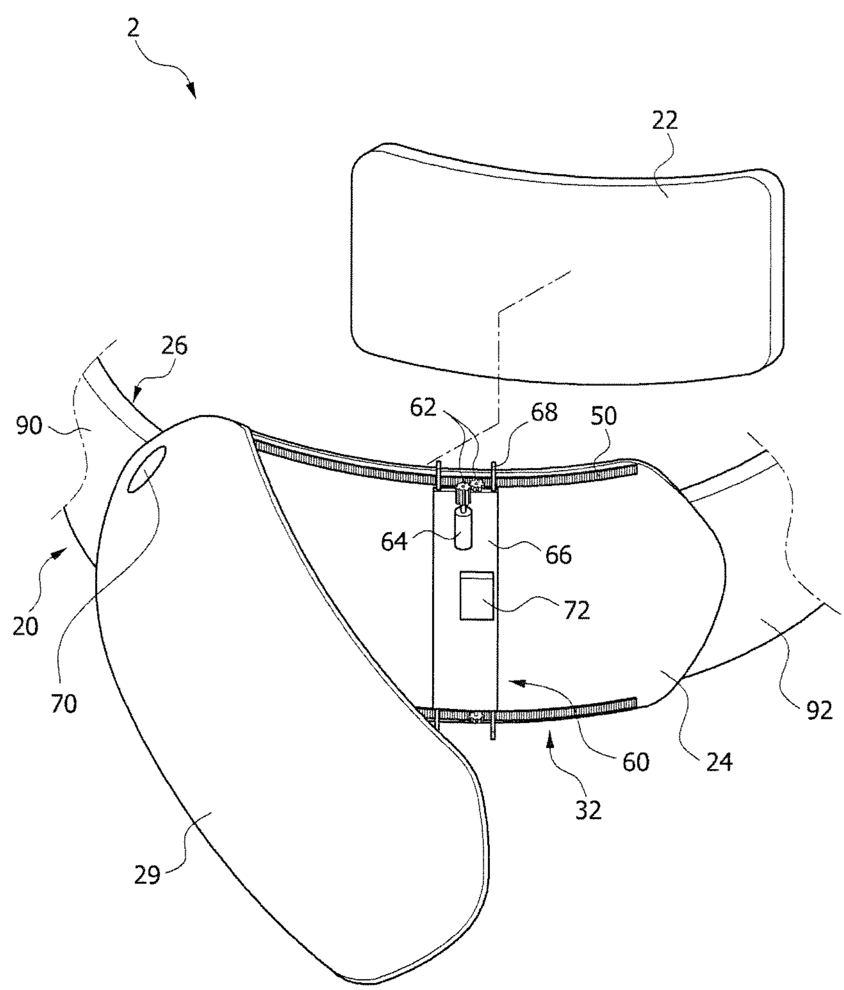
FIG. 7 is an exploded perspective view of an ultrasonic diagnostic apparatus according to a second embodiment of the present disclosure.
Figure 8:
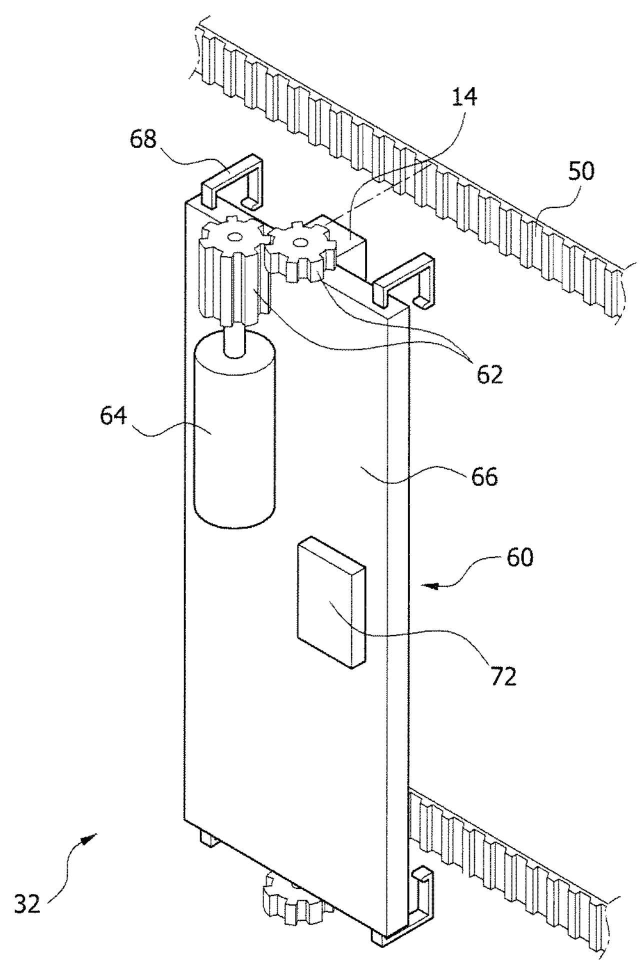
FIG. 8 is a perspective view of a mover of the ultrasonic diagnostic apparatus according to the second embodiment of the present disclosure.

FIG. 7 is an exploded perspective view of an ultrasonic diagnostic apparatus according to a second embodiment and FIG. 8 is a perspective view of a mover of the ultrasonic diagnostic apparatus according to the second embodiment.

Referring to FIGS. 7 and 8, a mover 32 of the ultrasonic diagnostic apparatus 2 according to this embodiment includes gear racks 50 disposed on a fastening part 20 in a longitudinal direction in which a probe 14 is moved, and a movable examination part 60 moving along the gear racks 50 and having the probe 14 secured to a side surface of the movable examination part 60.

The gear racks 50 are respectively secured to opposite sides of an ultrasound permeable film 24 and both of the gear racks 50 and the ultrasound permeable film 24 are made of a flexible material.

Since the gear racks 50 are disposed at the opposite sides of the movable examination part 60 including the probe 14 (in FIG. 7), the movable examination part 60 may be more stably moved in the longitudinal direction of the gear racks 50.

In the second embodiment, the movable examination part 60 includes pinion members 62, which engage with and rotate on the gear racks 50, a transport motor 64 driving the pinion members 62, a movable plate 66 on which the transport motor 64, pinion members 62 and probe 14 are mounted, and anti-separation rings 68 each bent at opposite sides of the movable plate 66 to catch lateral sides of the fastening part 20.

Each of the anti-separation rings 68 extends across the movable plate 66 and is bent at the opposite sides of the movable plate 66. Since both sides of each of the anti-separation rings 68 extend to and catch the rear side of the ultrasound permeable film 24, the anti-separation rings 68 prevent separation of the movable plate 66 from the movable examination part 60.

The movable plate 66 is provided with a motion controller 72, which controls operation of the transport motor 64 which rotates the pinion members 62 engaging with the gear racks 50.

One of the pinion members 62 may be disposed under the movable plate 66 to engage with and rotate on the gear rack 51.

Next, operation of the ultrasonic diagnostic apparatus 2 according to the second embodiment will be described with reference to the accompanying drawings.

When a user presses a button 70, power is supplied to the transport motor 64 to generate rotational power, which is transmitted to and rotates the pinion members 62 connected to the transport motor 64.

Since the pinion members 62 engage with and rotate on the gear racks 50, the movable plate 66 including the probe 14 is horizontally moved along the gear racks 50 (in FIG. 8).

The probe 14 attached to the movable plate 66 is also horizontally moved while scanning the neck 12 to generate thyroid ultrasound imagery.

The motion controller 72 calculates a current location of the probe 14 and adjusts rotation of the transport motor 64 in a forward or rearward direction to move the probe 14 in the longitudinal direction (in FIG. 8).

Next, an ultrasonic diagnostic apparatus 3 according to a third embodiment will be described with reference to the accompanying drawings.

For convenience of description, the same elements as those of the first embodiment will be denoted by the same reference numerals and elaboration thereof will be omitted herein.

Figure 9:
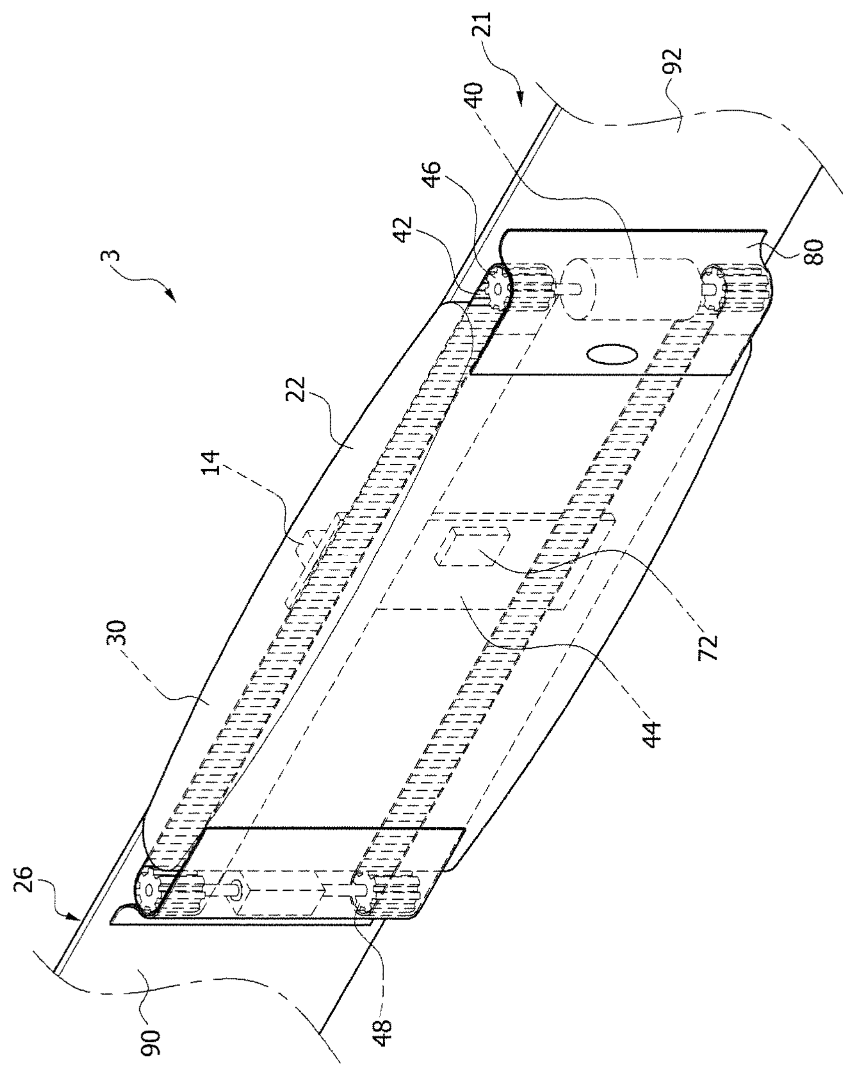
FIG. 9 is an exploded perspective view of an ultrasonic diagnostic apparatus according to a third embodiment of the present disclosure.
Figure 10:
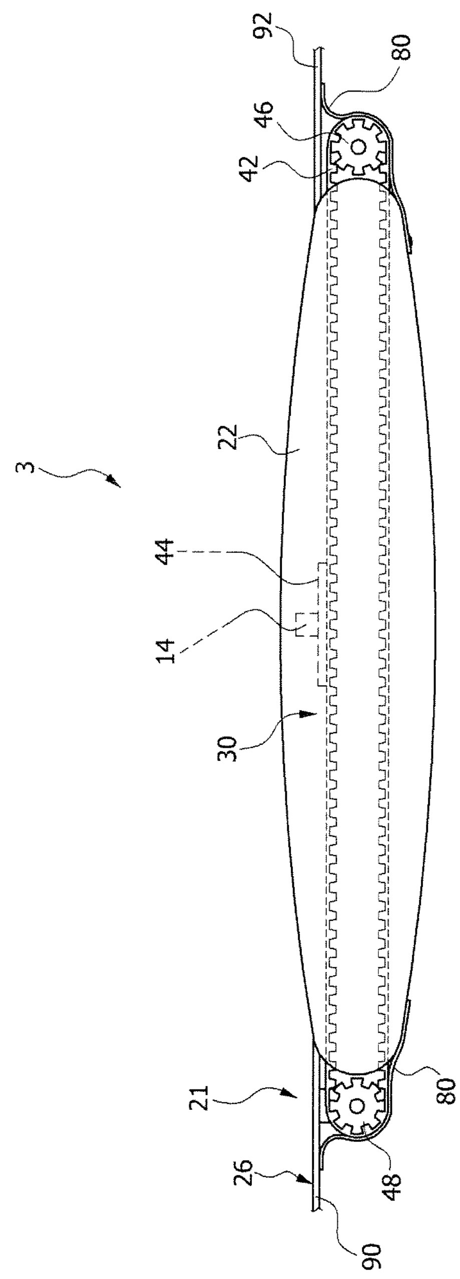
FIG. 10 is a plan view of the ultrasonic diagnostic apparatus of FIG. 9.
Figure 11:
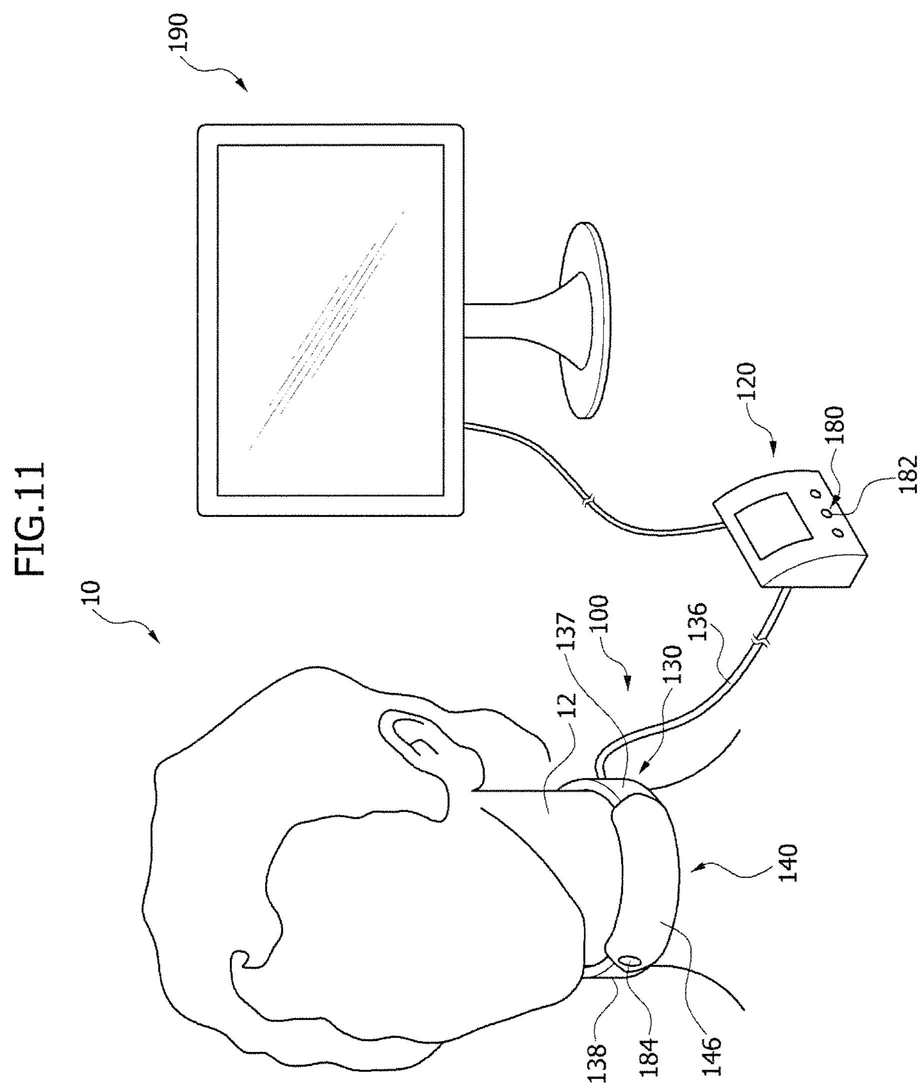
FIG. 11 is a perspective view of an ultrasonic diagnostic apparatus according to a fourth embodiment of the present disclosure in use.
Figure 12:
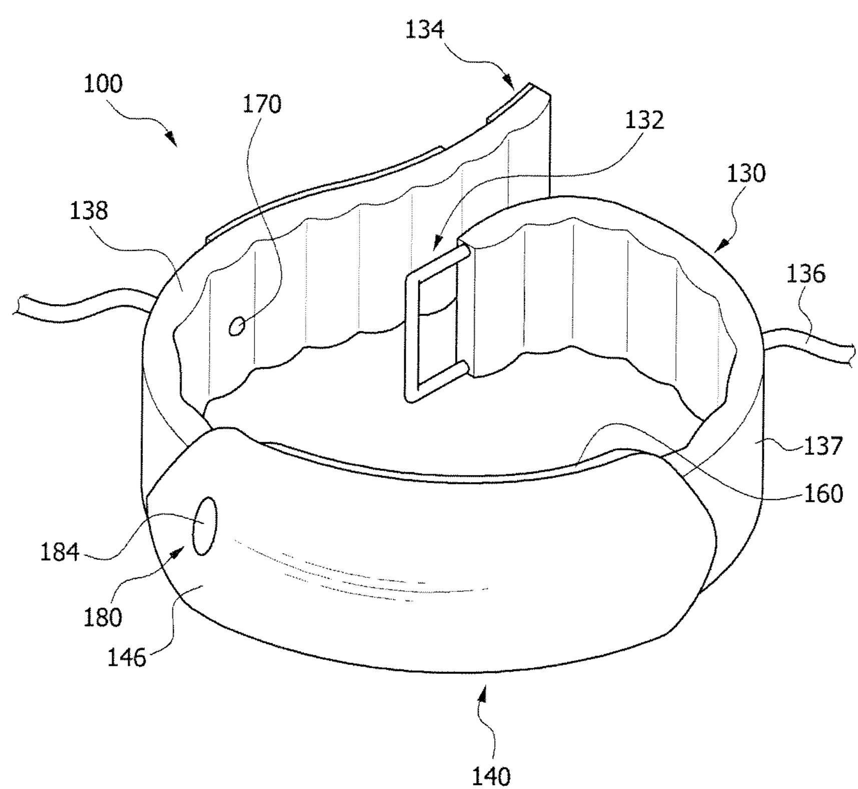
FIG. 12 is a perspective view of the ultrasonic diagnostic apparatus according to the fourth embodiment of the present disclosure.
Figure 13:
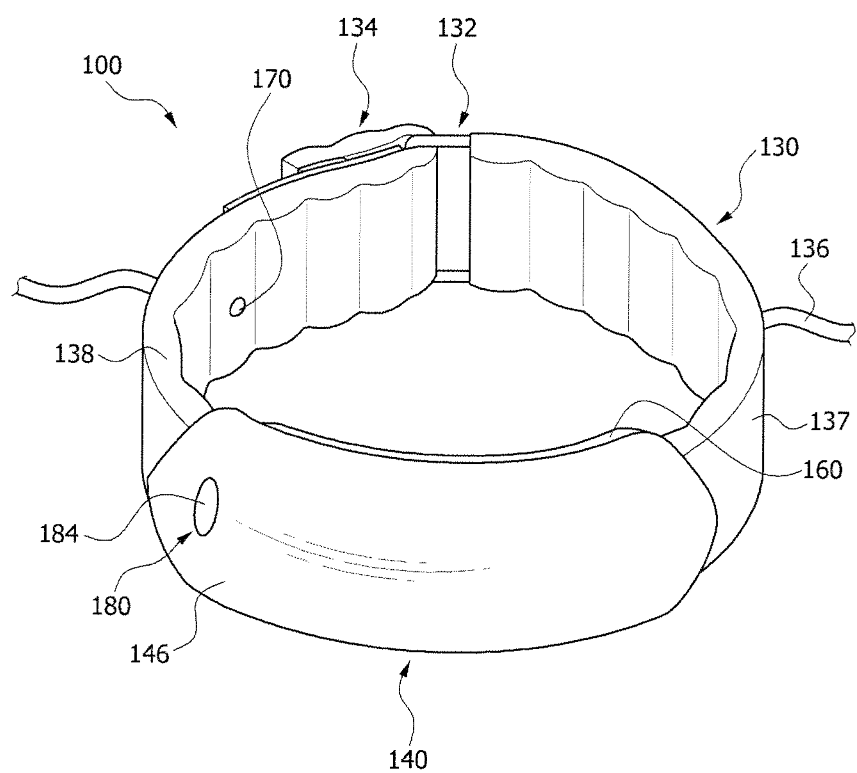
FIG. 13 is an exploded perspective view of the ultrasonic diagnostic apparatus of FIG. 12, showing a first fastener and a second fastener fastened to each other.
Figure 14:
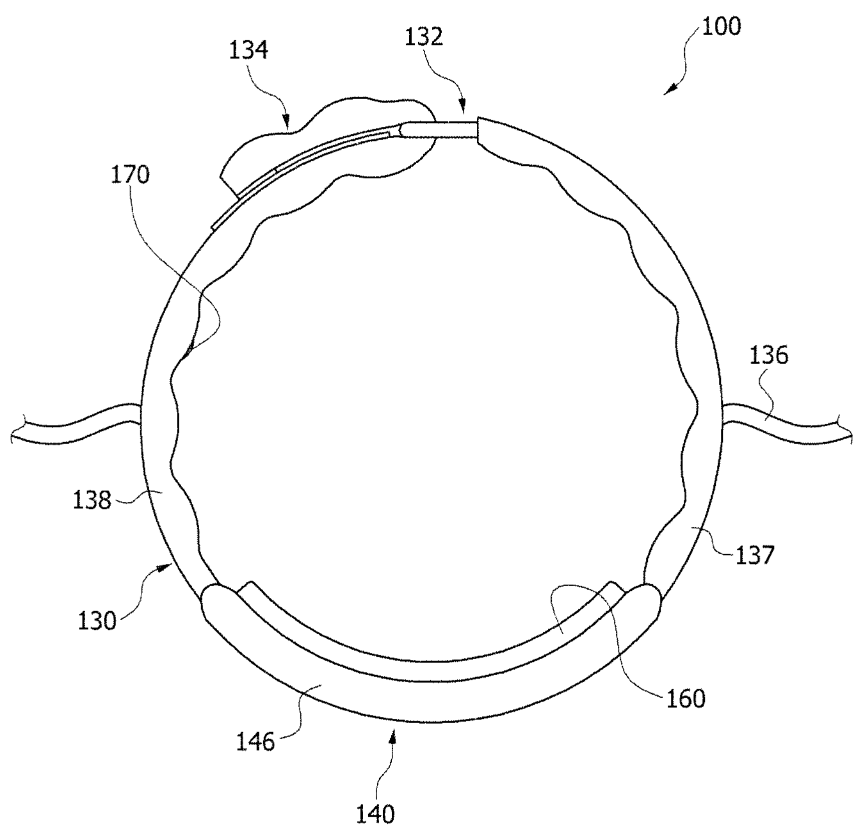
FIG. 14 is a plan view of the ultrasonic diagnostic apparatus according to the fourth embodiment of the present disclosure before hydraulic pressure is applied to a fluid expansion part.
Figure 15:
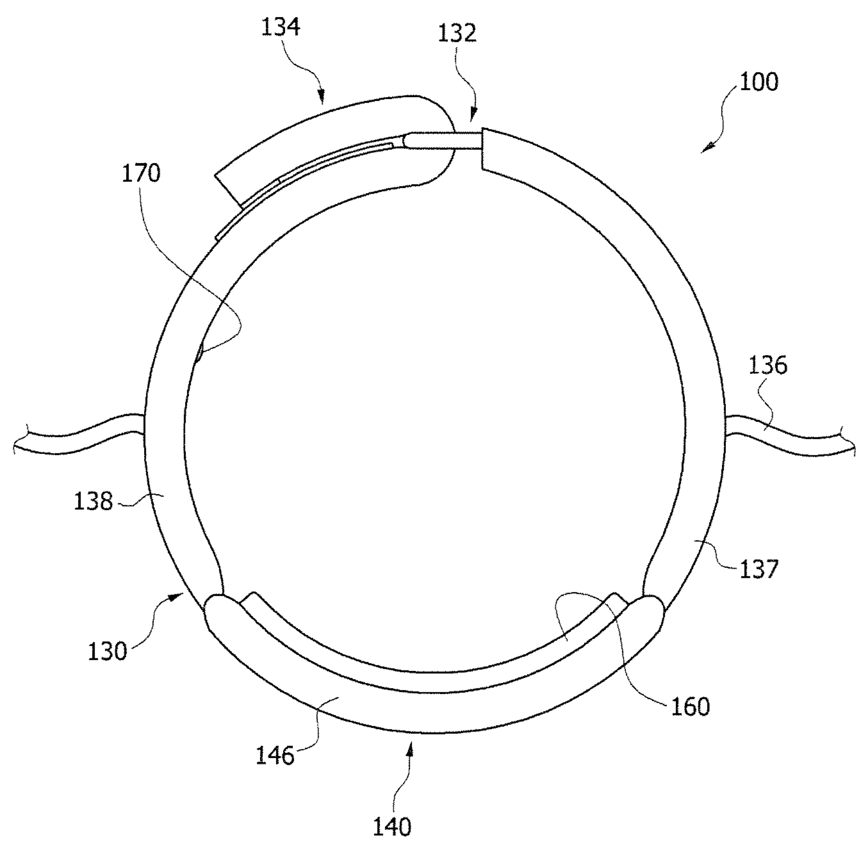
FIG. 15 is a plan view of the ultrasonic diagnostic apparatus according to the fourth embodiment of the present disclosure after hydraulic pressure is applied to the fluid expansion part.
Figure 16:
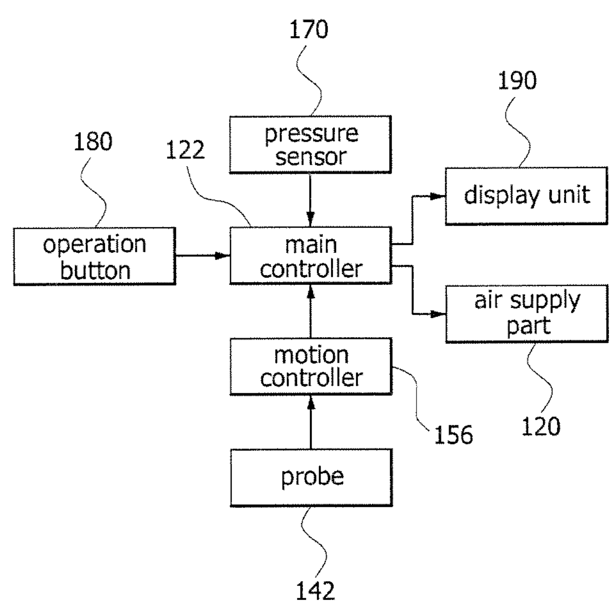
FIG. 16 is a block diagram of the ultrasonic diagnostic apparatus according to the fourth embodiment of the present disclosure.

FIG. 9 is an exploded perspective view of an ultrasonic diagnostic apparatus according to a third embodiment and FIG. 10 is a plan view of the ultrasonic diagnostic apparatus of FIG. 9.

Referring to FIGS. 9 and 10, in the ultrasonic diagnostic apparatus according to the third embodiment, a fastening part 21 includes a resilient gel pad 22 disposed in a moving direction of a mover 30 to surround the mover 30, and a band member 26 connected to the gel pad 22.

In the mover 30 of the ultrasonic diagnostic apparatus, conveyor belts 42 are disposed within the gel pad 22, and a movable mounting part 44 and a probe 14 moving along the conveyor belts 42 are also disposed within the gel pad 22.

A drive member 40, drive gears 46 and driven gears 48 are disposed outside or inside the gel pad 22 to rotate the conveyor belts 42.

The drive member 40, drive gears 46 and driven gears 48 disposed outside the gel pad 22 are encased in a side cover 80 to be isolated from the outside.

In the ultrasonic diagnostic apparatus 3 according to this embodiment, the ultrasound permeable film 24 and the cover 36 of the first embodiment are omitted, thereby reducing manufacturing costs.

Next, operation of the ultrasonic diagnostic apparatus 3 according to the third embodiment will be described with reference to the accompanying drawings.

When a user presses a button (not shown) on the fastening part 21, power is supplied to the drive member 40 to generate rotational power, which is transmitted to and rotates the drive gears 46 located at opposite sides of the drive member 40 (in FIG. 9).

Rotation of the drive gears 46 leads to rotation of the conveyor belts 42 between the drive gears 46 and the driven gears 48 within the gel pad 22.

Then, the movable mounting part 44 secured to the conveyor belts 42 is moved in conjunction with the conveyor belts 42 within the gel pad 22.

The probe 14 attached to the movable mounting part 44 is also horizontally moved while scanning the neck 12 to generate thyroid ultrasound imagery. Here, since only an ultrasound permeable gel is disposed between the probe 14 and the neck 12, it is possible to reduce measurement errors that can occur due to the formation of pockets of air therebetween.

The motion controller 72 calculates a current location of the probe 14 and adjusts rotation of the drive member 40 in a forward or rearward direction so as to allow the probe 14 to move within the gel pad 22.

Accordingly, in each of the ultrasonic diagnostic apparatuses 1, 2 or 3 according to the embodiments described above, the probe 14 mounted on the mover 30 or 32 provides consistent quality ultrasound images of the diagnosis object 10 while the mover 30 or 32 moves along the fastening part 20, 21 securely wound around the diagnosis object 10, thereby guaranteeing improved reliability of ultrasonic diagnosis.

In addition, since the probe 14 is automatically moved on the fastening part, the ultrasonic diagnostic apparatus may guarantee improved operability by reducing user fatigue.

Next, an ultrasonic diagnostic apparatus 100 according to a fourth embodiment will be described with reference to the drawings.

FIGS. 11 to 16 illustrate the ultrasonic diagnostic apparatus according to the fourth embodiment of the present disclosure.

In FIGS. 11 to 16, the ultrasonic diagnostic apparatus 100 according to the fourth embodiment includes a fluid supply part 120 which supplies hydraulic pressure, a band member 130 wound around a diagnosis object 10 and connected to the fluid supply part 120 to be expanded by the hydraulic pressure, and an examination part 140 connected to the band member 130.

In the fourth embodiment, the diagnosis object 10 is a person and the ultrasonic diagnostic apparatus 100 is wound around the neck 12 of the person for examination of the thyroid.

The examination part 140 is positioned in front of the thyroid and the probe 142 in the examination part 140 provides ultrasound imagery of the thyroid while moving along the neck 12.

The examination part 140 also includes an ultrasound permeable film and a mover that moves the probe 142 along the ultrasound permeable film. Here, since the configurations of the ultrasound permeable film and the mover are the same as those of the ultrasound permeable film 24 and the mover 30, 32 of the first and second embodiments, elaboration thereof will be omitted herein.

The fluid supply part 120 is connected to the band member 130 via a fluid tube 136, so that hydraulic pressure generated in the fluid supply part 120 is applied to the band member 130 through the fluid tube 136.

In the fourth embodiment, the ultrasonic diagnostic apparatus 100 is operated through manipulation of operation buttons 180, which include a first button 182 provided to the fluid supply part 120 and a second button 184 provided to the examination part 140.

With the first button 182 disposed on a front side thereof, the fluid supply part 120 includes a main controller 122 which is disposed in the fluid supply part 120 and controls the ultrasonic diagnostic apparatus 100.

The band member 130 configured to receive hydraulic pressure from the fluid supply part 120 includes a first band member 137 connected to one side of the examination part 140 and a second band member 138 connected to the other side of the examination part 140.

The band member 130 may further include a first fastener 132 connected to the first band member 137 and a second fastener 134 connected to the second band member 138 to be fastened to the first fastener 132. Any members may be employed as the first and second fasteners 132, 138 so long as the members can be fastened to each other.

In one embodiment, fabric hook-and-loop fasteners such as Velcro fasteners may be provided as the first and second fasteners 132, 138.

In the fourth embodiment, a ring member is used as the first fastener 132 and a fabric hook-and-loop fastener such as a Velcro fastener is used as the second fastener 134, thereby allowing easy adjustment in length and easy attachment/detachment of the band member 130.

The band member 130 may be modified in various ways. For example, the band member 130 may be connected to the opposite sides of the examination part 140 to surround the neck 12.

The first band member 137 and the second band member 138 are connected to the opposite sides of the examination part 140.

The examination part 140 is provided with a motion controller 156, which moves along with the probe 142 and is operated by manipulation of the second button 184 disposed on a cover 146 covering the motion controller 156.

The motion controller 156 is connected to the main controller 122 via wired or wireless communication to send an ultrasound signal of the probe 142 thereto, and the main controller 122 converts the ultrasound signal into an image signal and sends the image signal to a display unit 190.

The probe 142 is moved by manipulation of the second button 184 on the cover 146.

A gel pad 160 may be disposed to adjoin the examination part 140. Obviously, the ultrasonic diagnostic apparatus may use the examination part 140 without the gel pad 160. The gel pad 160 includes an ultrasound permeable gel therein When the probe 142 is used to examine the neck 12, the gel pad 160 is in close contact with the neck 12 along the circumference thereof, thereby preventing measurement errors caused by the formation of a gap between the probe 142 and the diagnosis object 10.

The ultrasonic diagnostic apparatus 100 is provided with a pressure sensor 170, which measures the degree of expansion of the band member 130 by operation of the fluid supply part 120 and sends the result to the motion controller 156.

The pressure sensor 170 measures the pressure of the band member 130 so as to prevent the band member 130 from exceeding a preset pressure when compressing the neck 12. The pressure sensor 170 may be placed at any suitable location, as needed. For example, the pressure sensor 170 may be disposed on an inner surface of the band member 140 contacting the neck 12 or inside the fluid supply part 120.

Various images including the measurement results of the pressure sensor 170 and the ultrasound images obtained through the examination part 140 are delivered to a display unit 190 through the main controller 122.

In one embodiment, any gas such as air, nitrogen or the like may serve as the fluid. Alternatively, a liquid material may serve as the fluid.

Next, operation of the ultrasonic diagnostic apparatus 100 according to the fourth embodiment will be described with reference to the accompanying drawings.

The band member 130 connected to the examination part 140 is wound around the neck 12 of the diagnosis object 10.

With the examination part 140 placed in front of the thyroid, the fabric hook-and-loop fastener provided as the second fastener 134 is inserted into the ring-shaped first fastener 132. After passing through the first fastener 132, the second fastener 134 is folded to obtain hook-and-loop fastening of the second fastener 134, so that the first fastener 132 and second fastener 134 are coupled to each other.

An operator selectively manipulates the first button 182 on the fluid supply part 120 and the second button 184 on the examination part 140 to operate the ultrasonic diagnostic apparatus 100.

When an operation signal is input through the operation buttons 180, the fluid supply part 120 is operated to generate hydraulic pressure, which in turn is supplied to the band member 130 through the fluid tube 136.

The band member 130 is expanded by the hydraulic pressure, thereby forcing the examination part 140 in the direction of the neck 12 and ensuring stable contact therewith.

When the pressure of the band member 130 measured by the pressure sensor 170 reaches a preset pressure or more, the operation of the fluid supply part 120 is stopped.

After the operation of the fluid supply part 120 is stopped, the probe 142 is automatically moved or operated by manipulation of the second button 184 to perform ultrasonic diagnosis.

With the configuration of the ultrasonic diagnostic apparatus 100 of the fourth embodiment as described above, the band member 130 is expanded so as to force the examination part 140 having the probe 142 in the direction of the diagnosis object 10, so that a gap is prevented from being formed between the probe 142 and the diagnosis object 10, thereby improving the reliability of the ultrasound imagery.

Next, an ultrasonic diagnostic apparatus 201 according to a fifth embodiment will be described with reference to the accompanying drawings.

For convenience of description, the same elements as those of the first embodiment will be denoted by the same reference numerals and elaboration thereof will be omitted herein.

FIGS. 17 to 24 illustrate the ultrasonic diagnostic apparatus according to the fifth embodiment of the present disclosure.

Referring to FIGS. 17 to 24, the ultrasonic diagnostic apparatus 201 according to the fifth embodiment includes a fastening part 240 having a band shape and wound around a diagnosis object 10, a first mover 270 which moves a probe 230 in a first direction 232 along the fastening part 240, and a second mover 290 which moves the probe 230 in a second direction 234 different from the first direction 232.

Figure 17:
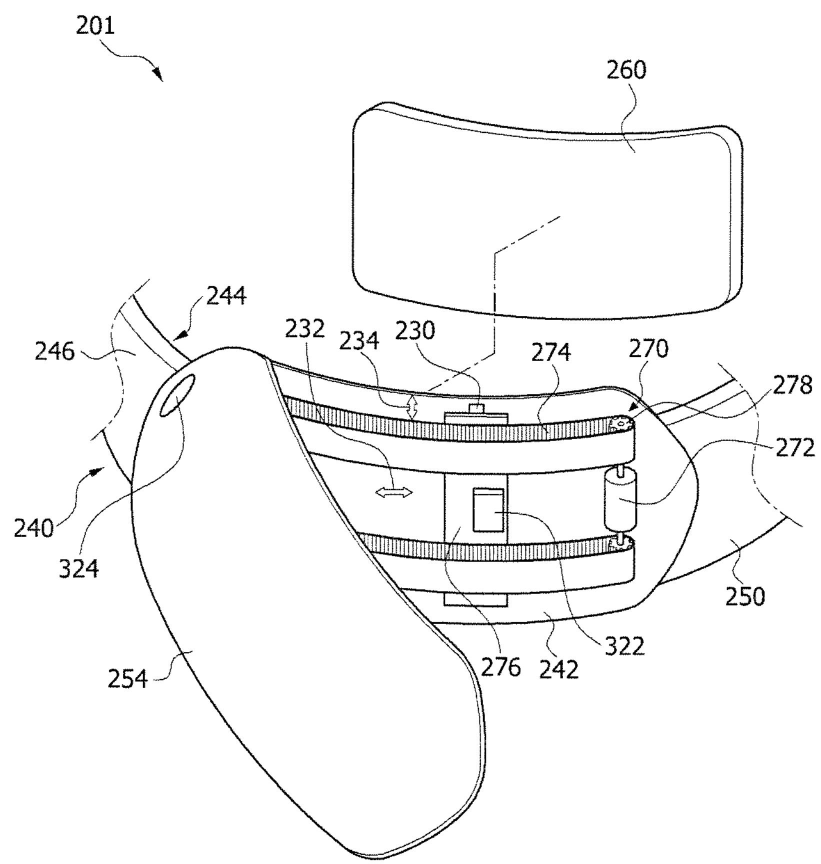
FIG. 17 is an exploded perspective view of an ultrasonic diagnostic apparatus according to a fifth embodiment of the present disclosure, showing a first mover in the ultrasonic diagnostic apparatus.

The first direction 232 is the moving direction of the probe 230 when the probe 230 is longitudinally moved by operation of the first mover 270 (in FIG. 17), and the second direction 234 is the moving direction of the probe 230 when the probe 230 is transversely moved by operation of the second mover 290 (in FIG. 17).

The first direction 232 and the second direction 234 are perpendicular to each other and the probe 230 provides ultrasound imagery of the diagnosis object 10 while moving in the first direction 232 or in the second direction 234. Although the first direction 232 and the second direction 234 are perpendicular to each other in this embodiment, it should be understood that the present disclosure is not limited thereto. Namely, the first direction 232 and the second direction 234 may be set to have any angle therebetween.

In the fifth embodiment, the diagnosis object 10 is a person and the ultrasonic diagnostic apparatus 201 is wound around the neck 12 of the person to examine the thyroid.

The fastening part 240 is wound around the neck 12 and the probe 230 provides ultrasound imagery of the thyroid while moving along the circumference of the neck 12.

Any device may serve as the probe 230 for the ultrasonic diagnostic apparatus 201 so long as the device can obtain ultrasound images of the diagnosis object 10 while transmitting or receiving ultrasound signals.

The fastening part 240 is wound around the diagnosis object 10, that is, the neck 12 of a person, and includes a first mover 270 and a second mover 290 disposed on a side surface of or inside the fastening part 240 to move the probe 230 automatically.

Any stretchable member such as a string or band may serve as the fastening part 240 or any expandable member may serve as the fastening part 240 so long as the member allows the first mover 270 and the second mover 290 to be placed at any suitable location facilitating acquisition of ultrasound imagery of the diagnosis object 10.

In the fifth embodiment, the fastening part 240 includes an ultrasound permeable film 242 disposed on the lateral side of the first mover 270 and a band member 244 connected to the ultrasound permeable film 242.

The ultrasound permeable film 242 may be made of any stretchable material that has high permeability to ultrasound waves and can be wrapped around the neck 12.

A gel pad 260 may be disposed to adjoin the ultrasound permeable film 242. Obviously, the ultrasonic diagnostic apparatus 201 may use the ultrasound permeable film 242 without the gel pad 260.

The gel pad 260 is provided to one side of the ultrasound permeable film 242 facing the diagnosis object 10 and includes an ultrasound permeable gel therein.

When the probe 230 is used to examine the neck 12, the gel pad 260 is in close contact with the neck 12 along the circumference thereof, thereby preventing measurement errors caused by the formation of a gap between the probe 230 and the diagnosis object 10.

The band member 244 includes a first band member 246 connected to one side of the ultrasound permeable film 242 and a second band member 250 connected to the other side of the ultrasound permeable film 242.

The band member 244 may further include a first fastener 48 connected to the first band member 246 and a second fastener 52 connected to the second band member 250 to be fastened to the first fastener 48. Any members may be employed as the first and second fasteners 48, 52 so long as the members can be fastened to each other.

In this embodiment, fabric hook-and-loop fasteners such as Velcro fasteners are provided as the first and second fasteners 48, 52, thereby allowing easy adjustment in length and easy attachment/detachment of the band member 244 to the object 10.

Any device may be employed as the first mover 270 of the ultrasound permeable film 242 so long as the device can move the probe 230 in a first direction 232 (longitudinal direction in FIG. 17).

Figure 19:
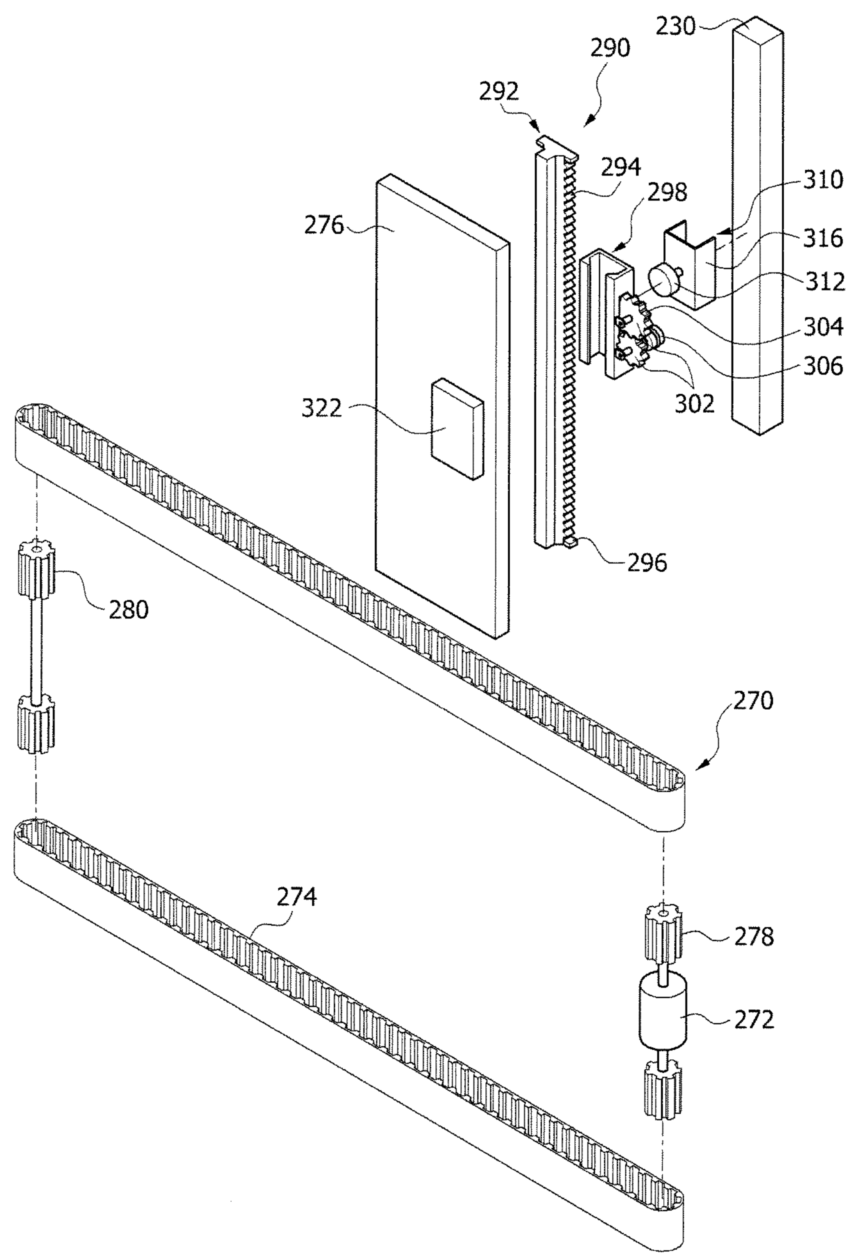
FIG. 19 is an exploded perspective view of the ultrasonic diagnostic apparatus according to the fifth embodiment of the present disclosure, showing a first mover, a second mover and a rotator in the ultrasonic diagnostic apparatus.

Referring to FIG. 19, the first mover 270 according to the fifth embodiment includes a first drive member 272 for supplying rotational power, conveyor belts 274 moved by rotational power from the first drive member 272, a movable mounting part 276 moved in conjunction with the conveyor belts 274 and having the probe 230 secured to one side thereof, a drive gear 278 powered by the first drive member 272 and supporting one side of each of the conveyor belts 274, and a driven gear 280 supporting the other side of each of the conveyor belts 274.

The first drive member 272 includes a motor for supplying rotational power and is secured to the ultrasound permeable film 242.

The drive gear 278 is coupled to either side of a shaft extending through the first drive member 272 in a vertical direction (in FIG. 19).

The drive gear 278 supports the one side (right side in FIG. 19) of each conveyor belt 274 and the driven gear 280 supports the other side (left side in FIG. 19) of each conveyor belt 274.

The driven gear 280 is also coupled to either side of a connection bar, which connects both driven gears 280 such that the driven gears 280 are simultaneously rotated.

The conveyor belt 274 has a threaded inner surface, which engages with the drive gear 278 and driven gear 280 to rotate therewith.

The movable mounting part 276 is secured to the conveyor belts 174 and moved in the first direction 232 as the conveyor belts 274 move in the first direction.

Since the conveyor belts 274 are disposed at opposite sides of the movable mounting part 276 (at upper and lower sides of the movable mounting part 276 in FIG. 17), the movable mounting part 276 may be more stably moved in the first direction 232.

The movable mounting part 276 is provided with a motion controller 322, which controls operations of the first drive member 272, the second drive member 306, a rotational motor 312, and the probe 230.

As shown in FIGS. 18 to 24, the motion controller 322 is controlled by an operation button 324, which may be disposed on a cover 254 covering the ultrasound permeable film 242.

The motion controller 322 is connected to a main controller 320 via wired or wireless communication to send an ultrasound signal of the probe 230 to the main controller 320, which in turn converts the ultrasound signal into an image signal and sends the image signal to a display unit 326.

The first mover 270, the second mover 290 and a rotator 310 are operated by manipulation of the operation button 324 on the cover 254. The first and second drive members 272, 306 and the rotational motor 312 are powered via wired or wireless communication or by a separate battery in the fastening part 240.

Figure 20:
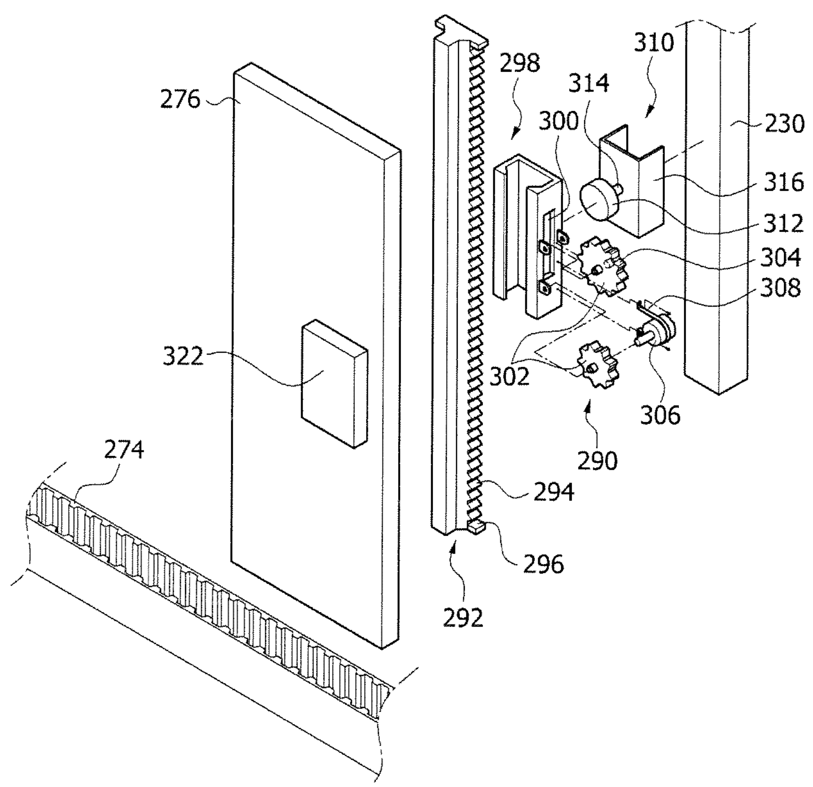
FIG. 20 is an exploded perspective view of a rotational gear and a second drive member detached from a movable bracket of FIG. 19.
Figure 21:
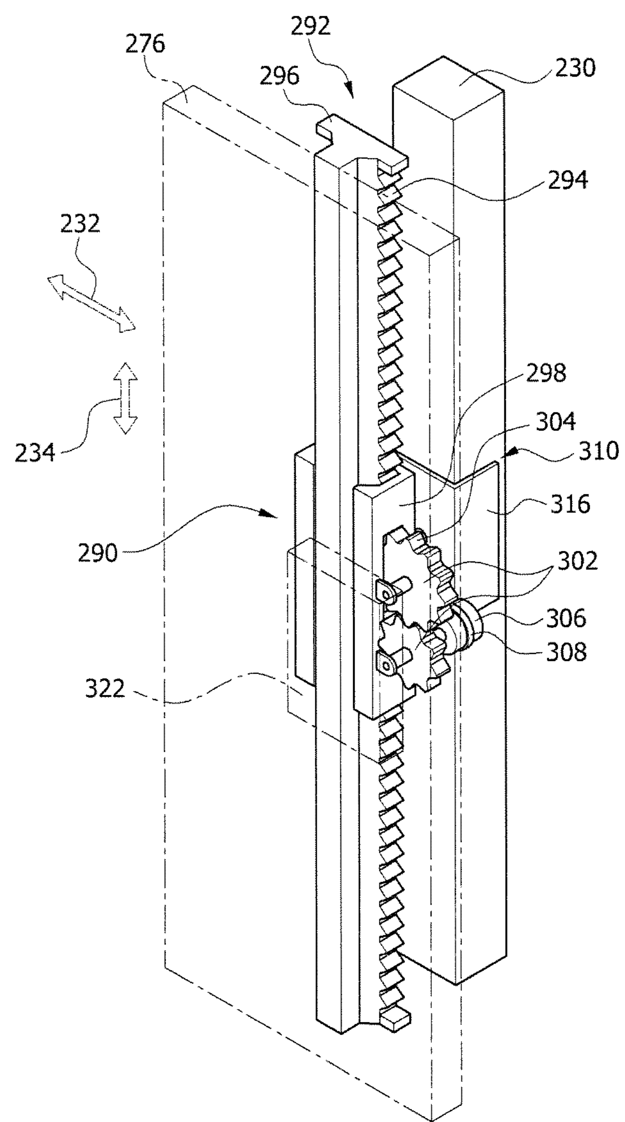
FIG. 21 is a perspective view of a probe disposed in the ultrasonic diagnostic apparatus according to the fifth embodiment of the present disclosure.

The second mover 290, which moves the probe 230 in the second direction 234, is mounted on the rear of the movable mounting part 276 (in FIG. 20).

In the fifth embodiment, the second mover 290 includes a guide rail 292 formed in the second direction 234 and having first teeth 294 formed on a side surface thereof, a movable bracket 298 moving along the guide rail 292, a rotational gear 302 formed on the movable bracket 298 and having second teeth 304 engaging with the first teeth 294, and a second drive member 306 rotating the rotational gear 302.

The guide rail 292 extends in the second direction 234 and is mounted on the rear of the movable mounting part 276. The guide rail 292 has stoppers 296 protruding from upper and lower sides thereof to prevent detachment of the movable bracket 298 moving along the guide rail 292.

The movable bracket 298 has a square pipe shape and is bent at opposite sides thereof to surround the first teeth 294 of the guide rail 292. The movable bracket 298 is formed at a side surface thereof with a connection hole 100, through which the first teeth 294 engage with the second teeth 304.

The second teeth 304 of the rotational gear 302 engage with the first teeth 294 of the guide rail 292 through the connection hole 100 to rotate together.

According to this embodiment, one or plural rotational gears 302 may be connected to the second drive member 306 and receive rotational power therefrom. The second drive member 306 is surrounded by a fixing bracket 308 and is fixed to the movable bracket 298.

The rotator 310 is mounted on the movable bracket 298 of the second mover 290 and rotates the probe 230 in response to a control signal from the motion controller 322.

In the fifth embodiment, the rotator 310 includes the rotational motor 312 for supplying rotational power and a rotational bracket 316 connected to an output shaft 314 of the rotational motor 312 while surrounding side surfaces of the probe 230.

The rotational bracket 316 is connected to the output shaft 314 of the rotational motor 312 and may have various shapes including a squared “C” shape to surround the probe 230.

Next, operation of the ultrasonic diagnostic apparatus 201 according to the fifth embodiment will be described with reference to the accompanying drawings.

With the fastening part 240 wound around the neck 12 of a diagnosis object 10, the probe 230 for transmitting and receiving ultrasound waves is placed on the neck 12 in which the thyroid is positioned.

The probe 230 is moved in the first direction 232 or the second direction 234 by manipulation of the operation button 324 while scanning the thyroid to generate thyroid ultrasound imagery.

When the probe 230 is moved in the first direction 232, power is supplied to the first drive member 272 under control of the motion controller 322 to generate rotational power. As the first drive member 272 is operated, the drive gears 278 located at the upper and lower sides of the first drive member 272 are rotated.

Rotation of the drive gears 278 leads to rotation of the conveyor belts 274 between the drive gears 278 and the driven gears 280.

The movable mounting part 276 secured to the conveyor belts 274 is also moved together with the conveyor belts 274, so that the probe 230 attached to the movable mounting part 276 is also moved in the first direction 232 while scanning the thyroid to generate thyroid ultrasound imagery.

Figure 18:
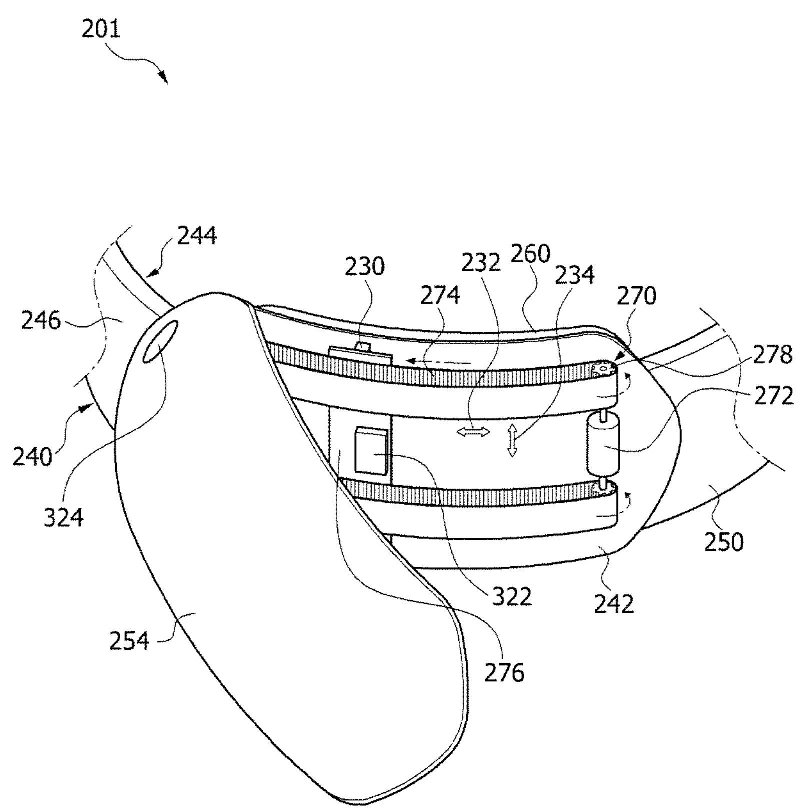
FIG. 18 is a perspective view of the ultrasonic diagnostic apparatus according to the fifth embodiment of the present disclosure, showing a movable mounting part that moves on conveyor belts in FIG. 17.

The motion controller 322 calculates a current location of the probe 230 and adjusts rotation of the first drive member 272 in a forward or rearward direction so as to move the probe 230 in the longitudinal direction (in FIG. 18).

Figure 22:
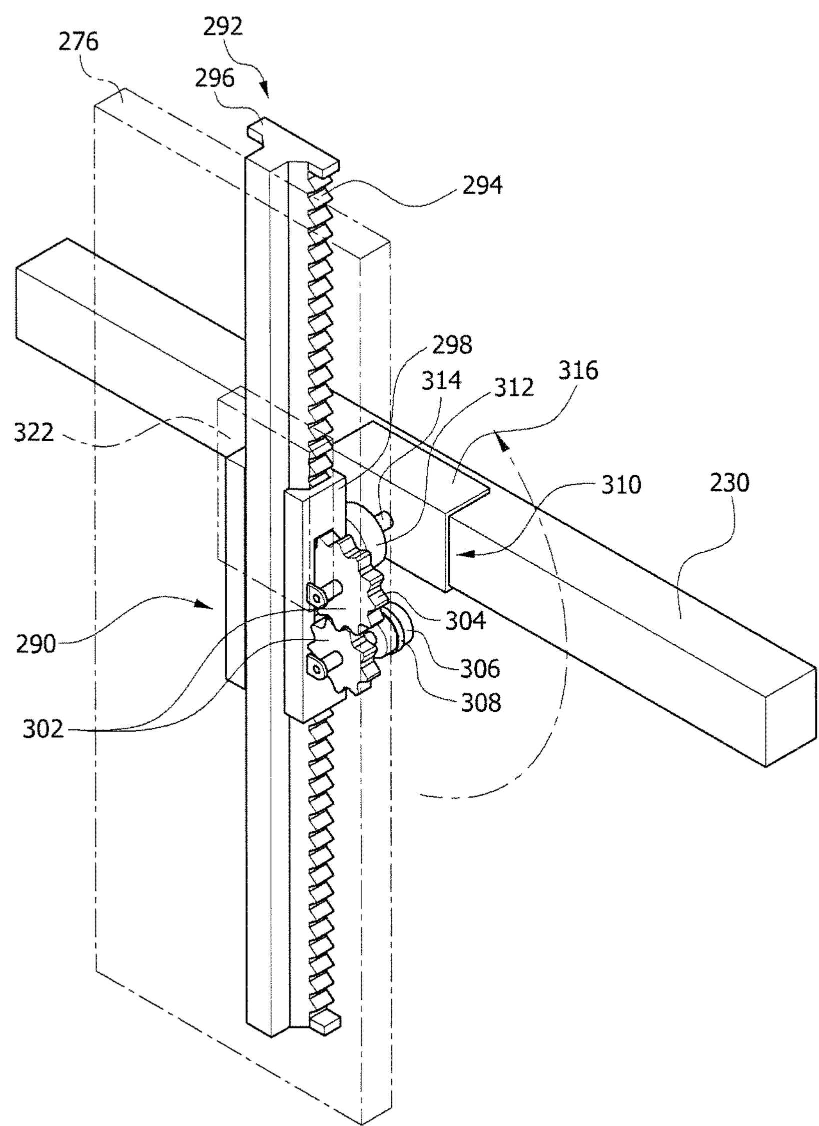
FIG. 22 is a perspective view of the probe of FIG. 21 when the probe is moved perpendicular to the guide rail.
Figure 23:
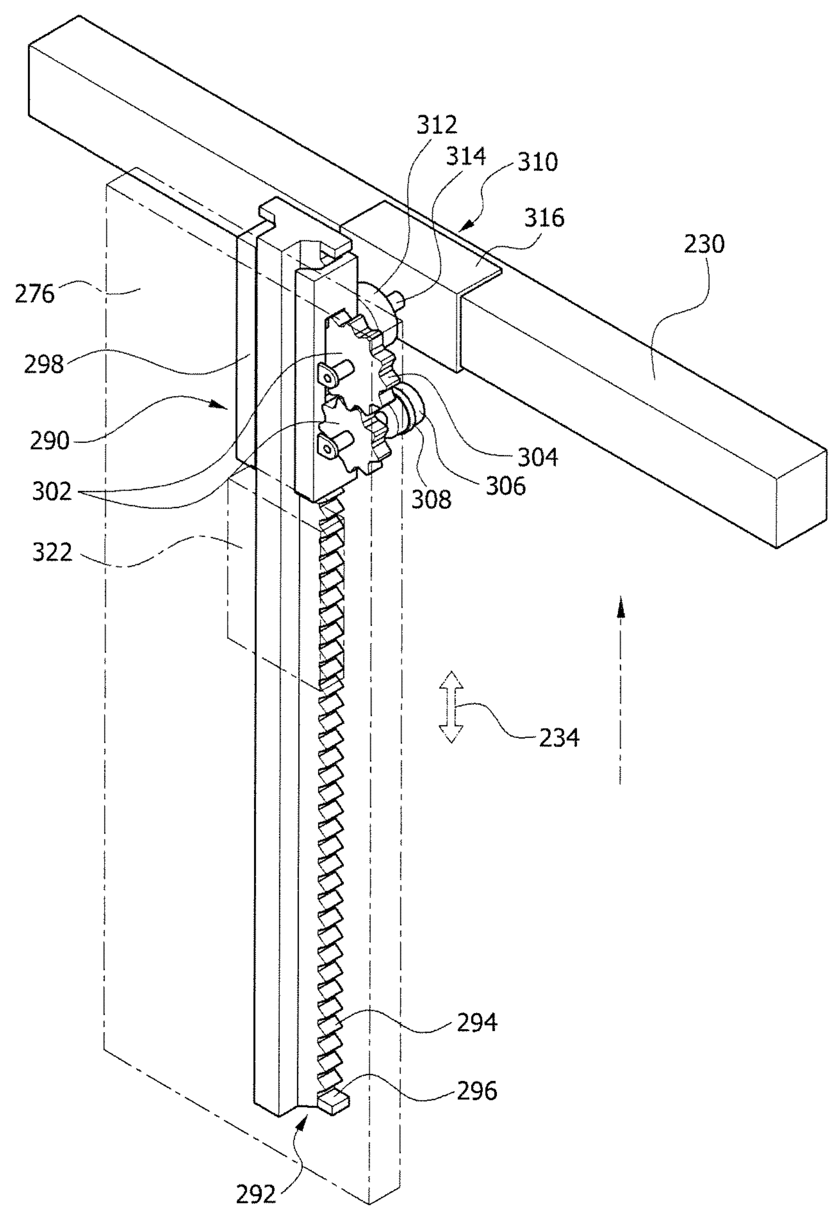
FIG. 23 is a perspective view of the probe of FIG. 22 when the probe is moved in a second direction.
Figure 24:
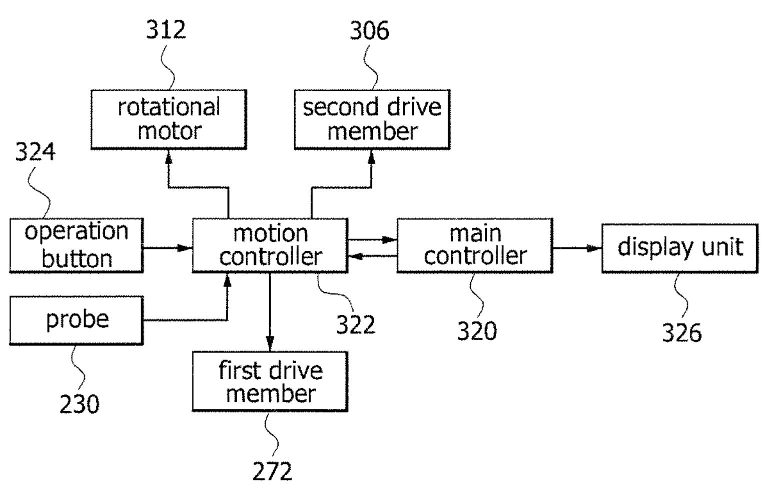
FIG. 24 is a block diagram of the ultrasonic diagnostic apparatus according to the fifth embodiment of the present disclosure.
Figure 25:
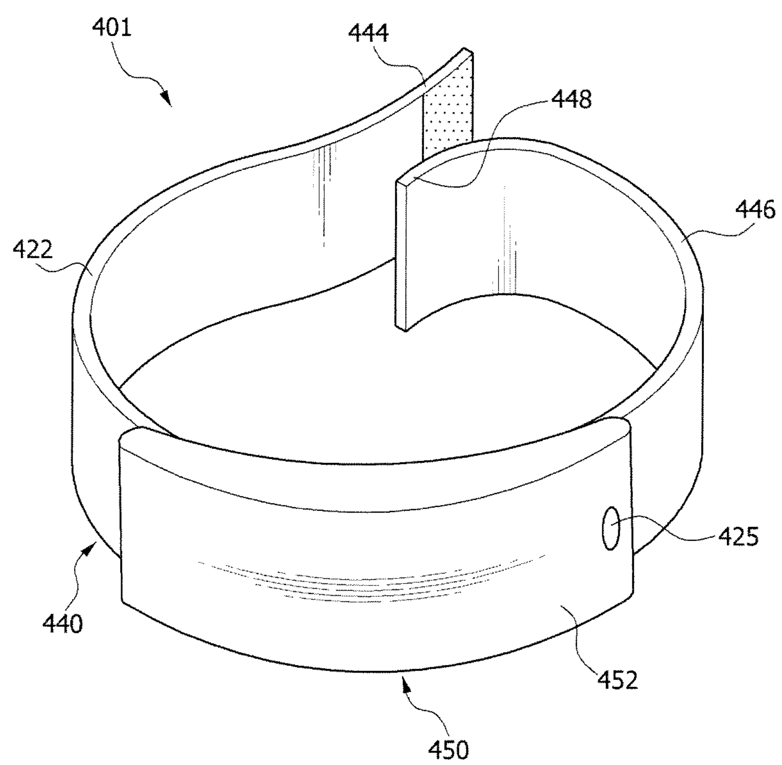
FIG. 25 is a perspective view of an ultrasonic diagnostic apparatus according to a sixth embodiment of the present disclosure.
Figure 26:
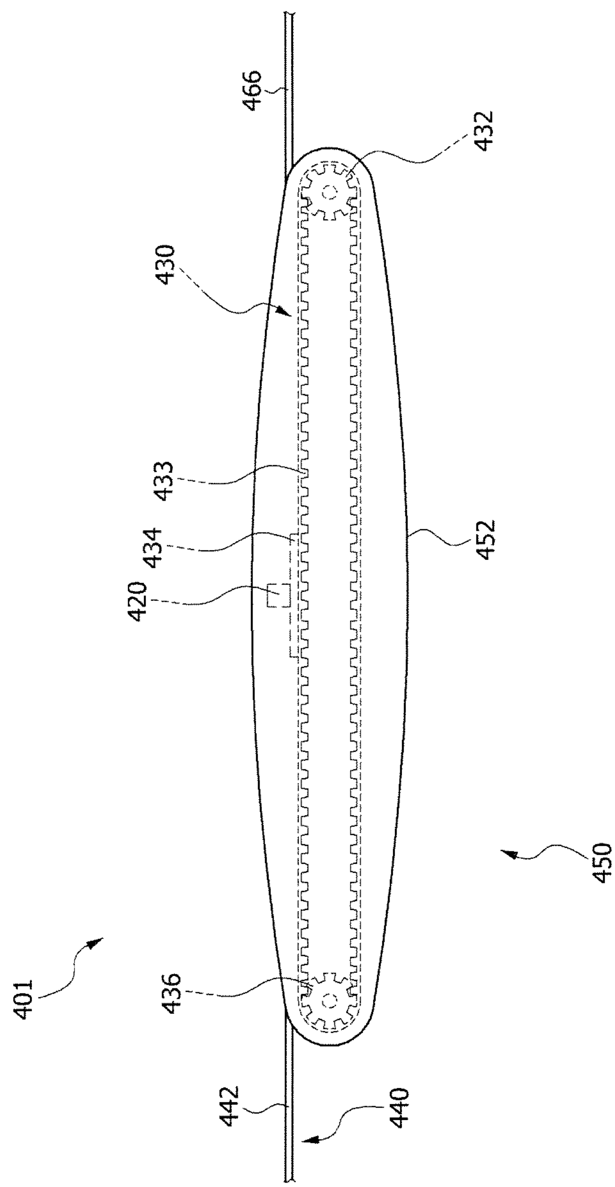
FIG. 26 is a plan view of a mover of the ultrasonic diagnostic apparatus according to the sixth embodiment of the present disclosure.

When the probe 230 is moved in the second direction 234, as shown in FIG. 22, power is supplied to the rotational motor 312 to generate rotational power under control of the motion controller 322.

As the rotational bracket 316 connected to the output shaft 314 of the rotational motor 312 is rotated, the probe 230 is also horizontally moved (in FIG. 22).

When the rotation of the probe 230 is completed, the second drive member 306 is operated to rotate the rotational gears 302, so that the second teeth 304 of the rotational gears 302 engage with the first teeth 294 of the guide rail 292 to rotate together, thereby moving the movable bracket 298 in the second direction 234.

As the movable bracket 298 is moved in the vertical direction, the probe 230 is also vertically moved while scanning the thyroid to generate thyroid ultrasound imagery.

Then, an ultrasound signal is transmitted from the probe 230 to the main controller 320 via the motion controller 322. Then, the main controller 320 converts the ultrasound signal into an image signal and sends the image signal to a display unit 326, thereby providing thyroid ultrasound imagery.

Accordingly, in the ultrasonic diagnostic apparatus according to the fifth embodiment described above, the probe 230 mounted on the mover 30 or 32 provides consistent quality ultrasound images of the diagnosis object 10 while the first mover 270 moves along the fastening part 240 securely wrapped around the diagnosis object 10, thereby guaranteeing improved reliability of ultrasonic diagnosis.

Further, in the fifth embodiment, the probe 230 is horizontally moved along the first mover 270 and vertically moved along the second mover 290, thereby providing more accurate ultrasound images than when configured to move in only one direction.

Further, in the ultrasonic diagnostic apparatus of the fifth embodiment, the first mover 270 and the second mover 290 may be operated to adjust the location of the probe corresponding to different locations of the thyroids of individuals.

Next, an ultrasonic diagnostic apparatus 401 according to a sixth embodiment will be described with reference to the accompanying drawings.

For convenience of description, the same elements as those of the first embodiment will be denoted by the same reference numerals and elaboration thereof will be omitted herein.

FIGS. 25 to 29 illustrate the ultrasonic diagnostic apparatus according to the sixth embodiment of the present disclosure.

As shown in FIGS. 25 to 29, the ultrasonic diagnostic apparatus 401 according to the sixth embodiment includes a probe 420 for probing a diagnosis object 10, a gel pad part 450 to be brought into contact with the diagnosis object 10, and a band member 440 connected to the gel pad part 450 and wound around the diagnosis object 10.

In the sixth embodiment, the diagnosis object 10 is a person and the ultrasonic diagnostic apparatus 401 is wrapped around the neck 12 of the person to examine the thyroid in the neck.

The gel pad part 450 and the band member 440 are configured to be wound around the neck 12, so that the probe 420 disposed inside the gel pad part 450 performs ultrasound examination of the thyroid while moving along the circumference of the neck 12.

Any device may serve as the probe 420 for the ultrasonic diagnostic apparatus 401 so long as the device can obtain ultrasound images of the diagnosis object 10 while transmitting or receiving ultrasound signals.

The probe 420 and a mover 430 for automatically moving the probe 420 are disposed within the gel pad part 450. The gel pad part 450 is kept in close contact with the diagnosis object 10 to prevent a gap from being formed between the probe 420 and the diagnosis object 10. Any member may serve as the gel pad part 450 so long as the member can provide such a function of the gel pad part 450 according to this embodiment.

In the sixth embodiment, the gel pad part 450 includes a gel pad 452, which is connected at both sides thereof to the band member 440.

When the probe 420 is used to examine the neck 12, the gel pad 452 is in close contact with the neck 12 along the circumference thereof, thereby preventing measurement errors caused by the formation of a gap between the probe 420 and the diagnosis object 10.

Any device may be employed as the mover 430 for the ultrasound permeable film 401 so long as the device can move the probe 230 within the gel pad 452.

In the sixth embodiment, the mover 430 includes a drive member 432 for supplying rotational power, conveyor belts 433 moved by rotational power from the drive member 432, a movable mounting part 434 moved in conjunction with the conveyor belts 433 and having the probe 420 secured to one side thereof, a drive gear 435 powered by the drive member 432 and supporting one side of each conveyor belt 433, and a driven gear 280 supporting the other side of each conveyor belt 433.

The drive member 432 includes a motor for supplying rotational power and is secured to an inner side of the gel pad 452.

Figure 29:
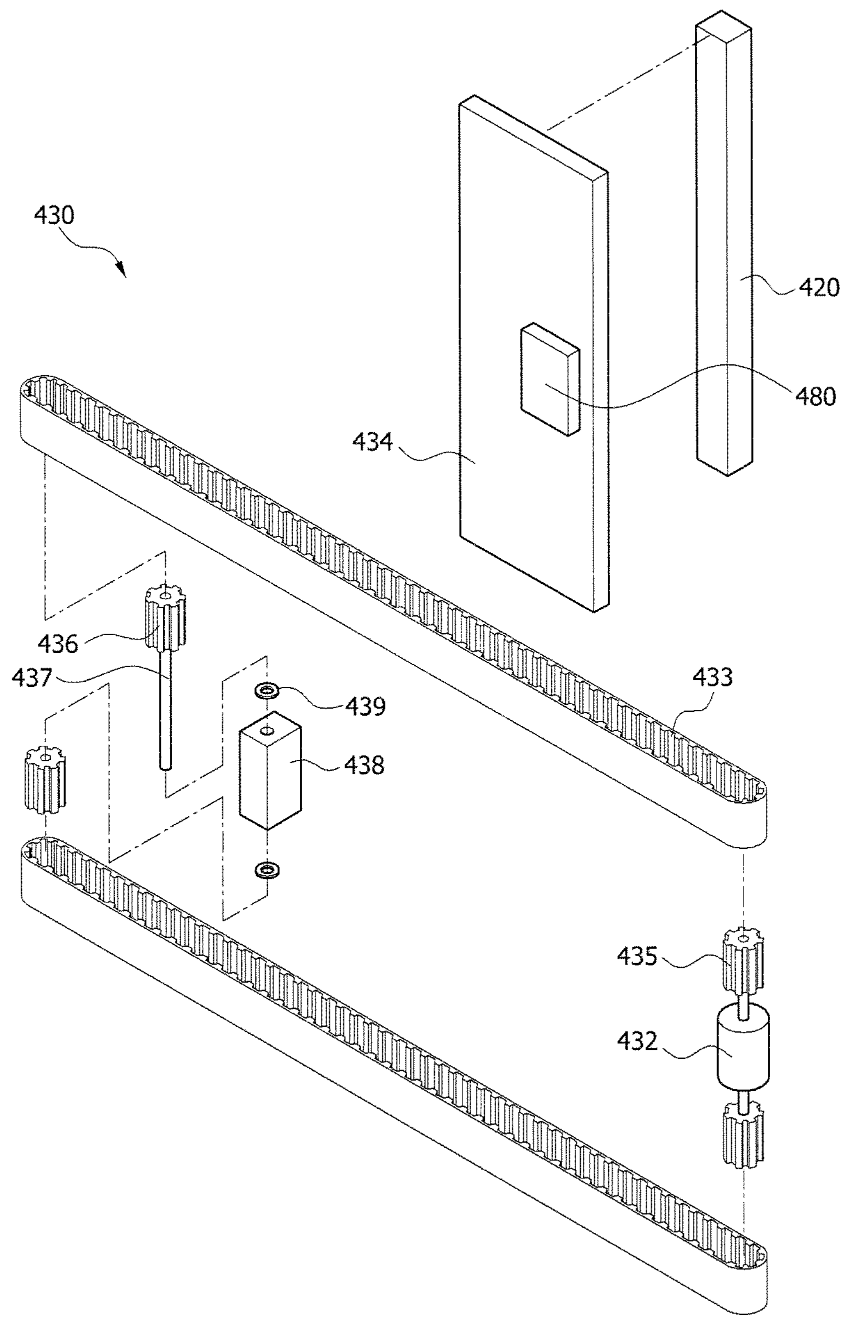
FIG. 29 is an exploded perspective view of the mover according to the sixth embodiment of the present disclosure.

The drive gear 435 is coupled to either side of a shaft extending through the drive member 432 in a vertical direction (in FIG. 29).

The drive gear 435 supports the one side (right side in FIG. 29) of each conveyor belt 433 and the driven gear 436 supports the other side (left side in FIG. 29) of each conveyor belt 433.

The driven gear 436 is also coupled to either side of a connection bar 437, which connects both driven gears 436 such that the driven gears 436 are simultaneously rotated.

The connection bar 437 penetrates a mounting bracket 438 and ring-shaped restriction members 439 are secured to the connection bar 437.

The mounting bracket 438 is secured to a side surface of the gel pad 452 to allow stable rotation of the driven gears 436 and the restriction members 439 are secured to the connection bar 437 to restrict vertical movement of the connection bar 437.

The conveyor belt 433 has a threaded inner surface, which engages with the drive gear 435 and driven gear 436 to rotate therewith.

A movable mounting part 434 having a plate shape is secured to the conveyor belts 433, so that the movable mounting part 434 having the probe 420 mounted thereon is moved in unison with the conveyor belts 433.

Figure 27:
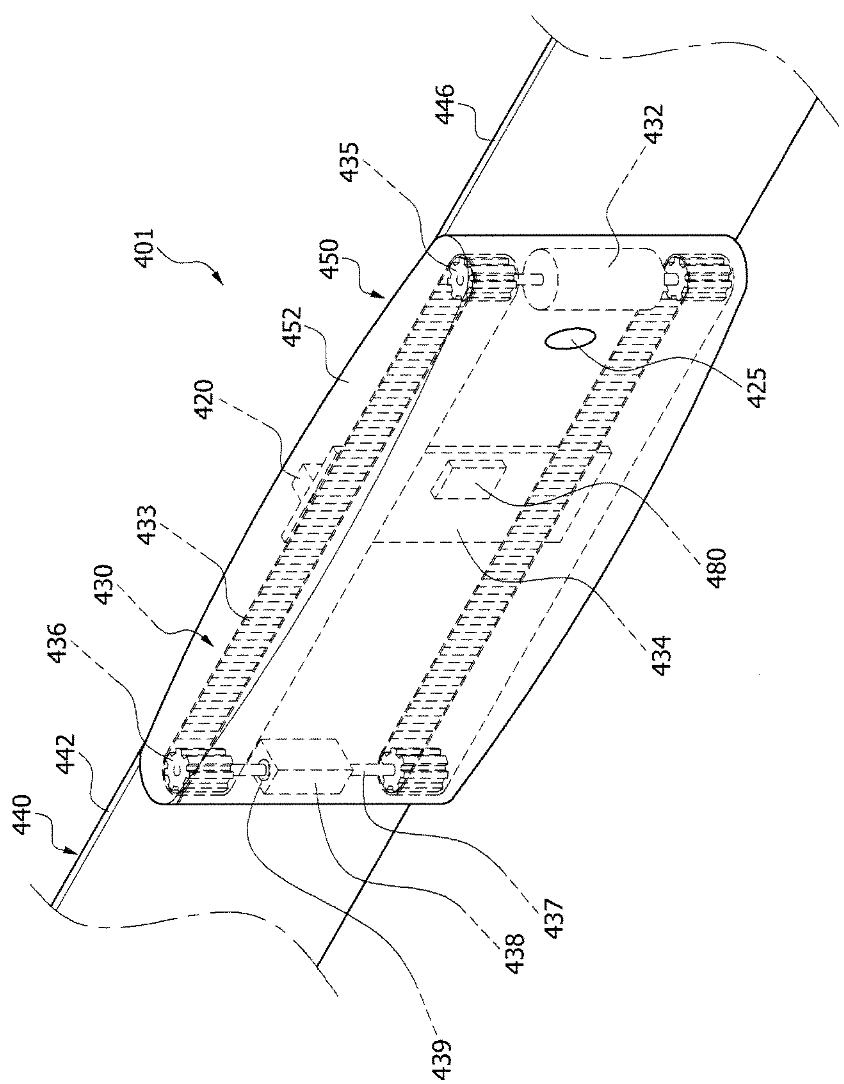
FIG. 27 is a perspective view of the mover of the ultrasonic diagnostic apparatus according to the sixth embodiment of the present disclosure.
Figure 28:
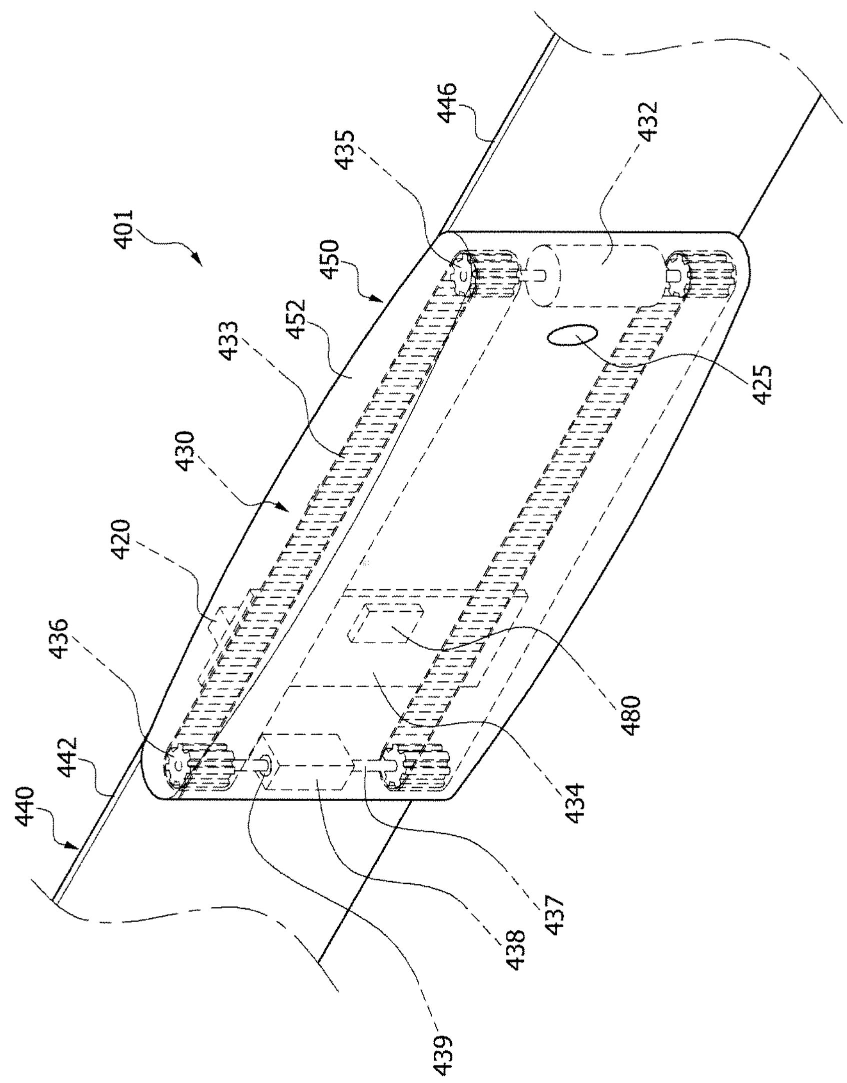
FIG. 28 is a perspective view of a probe of FIG. 27, which moves along conveyor belts.

To guarantee more stable movement of the movable mounting part 434, the conveyor belts 433 are disposed at opposite sides of the movable mounting part 434 (at upper and lower sides of the movable mounting part 434 in FIG. 27).

The movable mounting part 434 is provided with a motion controller 480, which controls operations of the drive member 432 and the probe 420.

The motion controller 480 is operated by a button 425, which may be provided to the gel pad 452 or the band member 440.

The motion controller 480 is connected to a main controller 74 via wired or wireless communication to send an ultrasound signal of the probe 420 to the main controller 74, which in turn converts the ultrasound signal into an image signal and sends the image signal to a display unit 76.

In the sixth embodiment, the ultrasonic diagnostic apparatus 401 selectively includes at least one of the motion controller 480 and the main controller 74.

The drive member 432 and the motion controller 480 may be powered via wired or wireless communication or by a separate battery in the gel pad 452 or the band member 440.

Any stretchable member such as a string or band may be employed as the band member 440 so long as the member allows the mover 430 to be positioned at any suitable location facilitating acquisition of the ultrasound imagery of the diagnosis object 10.

The band member 440 may include a first band member 442 connected to one side of the gel pad part 450 and a second band member 446 connected to the other side of the gel pad part 450.

The band member 440 may further include a first fastener 444 connected to the first band member 442 and a second fastener 448 connected to the second band member 446 to be fastened to the first fastener 444. Any members may be employed as the first and second fasteners 444, 448 so long as the members can be fastened to each other.

In the sixth embodiment, fabric hook-and-loop fasteners such as Velcro fasteners are provided as the first and second fasteners 444, 448, thereby allowing easy adjustment in length and easy attachment/detachment of the band member 440 to the object 10.

Next, operation of the ultrasonic diagnostic apparatus 401 according to the sixth embodiment will be described with reference to the accompanying drawings.

After the band member 440 connected to the gel pad part 450 is wound around the neck 12 of a diagnosis object 10, the first fastener 444 is fastened to the second fastener 448 to secure the location of the gel pad part 450 with respect to the neck 12.

The probe 420 is moved within the gel pad part 450 by manipulation of the button 425 while scanning the thyroid to generate thyroid ultrasound imagery.

Then, a signal is transmitted to the motion controller 480 by manipulation of the button 425 and power is supplied to the drive member 432 under control of the motion controller 480 to generate rotational power. As the drive member 432 is operated, the drive gears 435 located at the upper and lower sides of the drive member 432 are rotated.

Rotation of the drive gears 435 leads to rotation of the conveyor belts 433 between the drive gear 435 and the driven gear 436.

The movable mounting part 434 secured to the conveyor belts 433 is also moved together with the conveyor belts 433, so that the probe 420 attached to the movable mounting part 434 is also moved in the moving direction of the conveyor belts 433 while scanning the thyroid to generate thyroid ultrasound imagery.

The main controller 74 or the motion controller 480 calculates a current location of the probe 420 and adjusts rotation of the drive member 432 in a forward or rearward direction so as to move the probe 420 in the longitudinal direction (FIG. 27).

Since the gel pad 452 surrounding the mover 430 is disposed to surround the neck 12 having a curved shape, it is possible to reduce measurement errors that can occur due to the formation of pockets of air between the probe 420 and the diagnosis object 10 during ultrasonic diagnosis.

Then, ultrasound signals are transmitted from the probe 420 to the main controller 74 via the motion controller 480. Then, the main controller 74 converts the ultrasound signals into image signals and sends the image signals to a display unit 76, thereby providing thyroid ultrasound imagery.

Next, an ultrasonic diagnostic apparatus 402 according to a seventh embodiment will be described with reference to the accompanying drawings.

For convenience of description, the same elements as those of the first embodiment will be denoted by the same reference numerals and elaboration thereof will be omitted herein.

Figure 30:
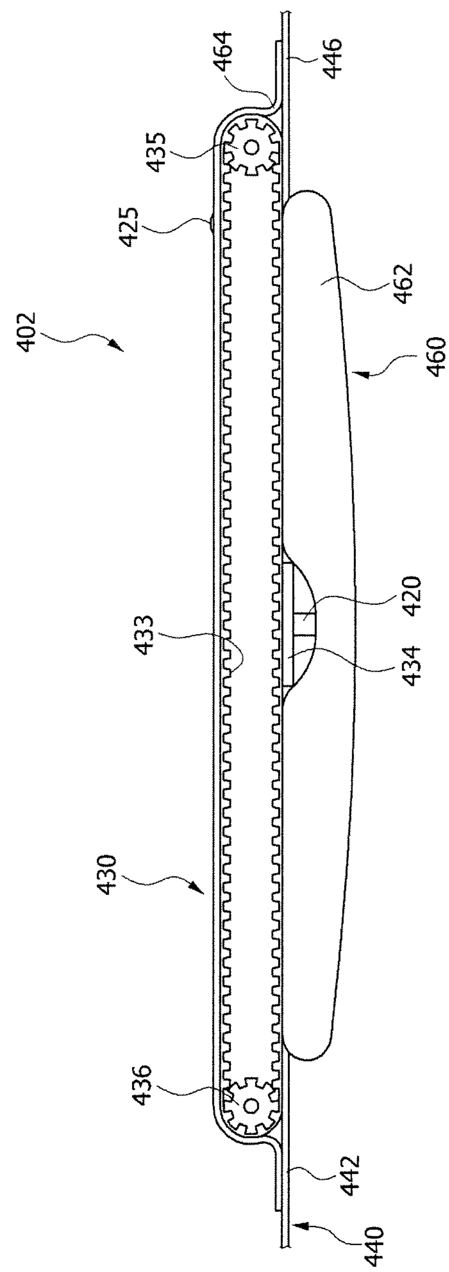
FIG. 30 is a plan view of a mover of an ultrasonic diagnostic apparatus according to a seventh embodiment of the present disclosure.
Figure 31:
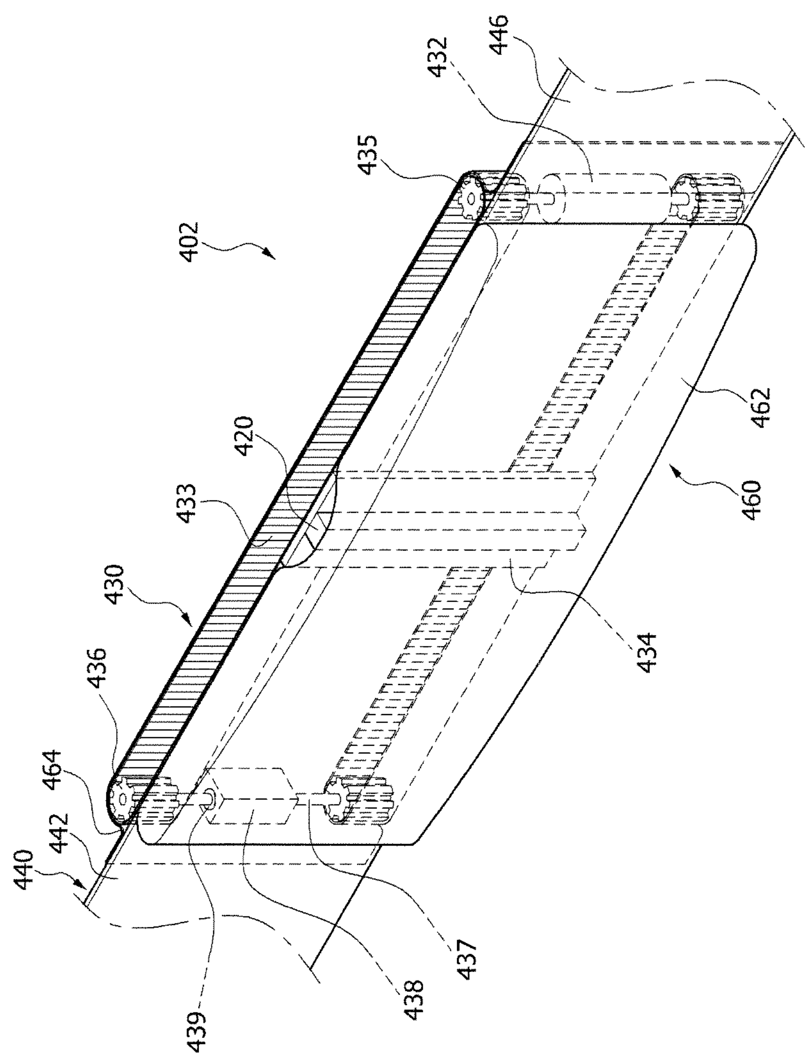
FIG. 31 is a perspective view of the mover of the ultrasonic diagnostic apparatus according to the seventh embodiment of the present disclosure.
Figure 32:
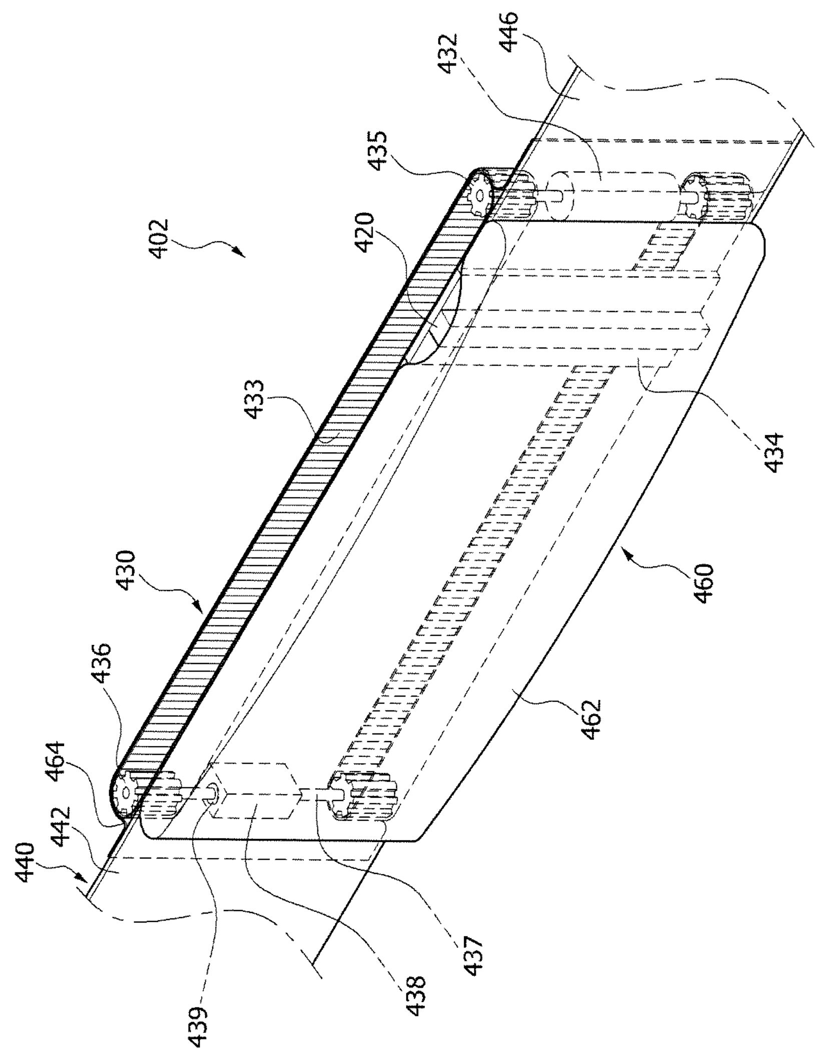
FIG. 32 is a perspective view of a probe of FIG. 29, which moves along conveyor belts.

FIG. 30 is a plan view of a mover of the ultrasonic diagnostic apparatus according to the seventh embodiment; FIG. 31 is a perspective view of the mover of the ultrasonic diagnostic apparatus according to the seventh embodiment; and FIG. 32 is a perspective view of a probe of FIG. 29, which moves along conveyor belts.

Referring to FIGS. 30 to 31, the ultrasonic diagnostic apparatus 402 according to the seventh embodiment includes a gel pad part 460 disposed to adjoin a side surface of a mover 430.

The gel pad part 460 includes a gel therein and adjoins a probe 420 moving together with a movable mounting part 434. Thus, the gel pad part 460 is longitudinally disposed along a movement path of the probe 420.

An exterior member 464 covers the mover 430 to protect the mover 430 from the outside. The exterior member 464 is provided with a button 425 which is used to control the mover 430.

In the ultrasonic diagnostic apparatus 402 according to the seventh embodiment, the probe 420 is moved in a state of adjoining the gel pad part 460 by operation of the mover 430 when probing the diagnosis object 10.

Accordingly, a gel pad 462 is disposed between the probe 420 and a body surface of the diagnosis object 10, so that a difference in acoustic impedance between the probe 420 and the body surface can be gradually reduced to prevent attenuation of acoustic signals, thereby improving the quality of the ultrasound imagery.

Furthermore, the gel pad 462 is disposed between the probe and the diagnosis object, so that a Fresnel Zone created near the probe and having a complex ultrasonic field due to non-uniform acoustic signal intensity is distant from the diagnosis object, thereby improving the quality of the ultrasound imagery.

As such according to the embodiments of the present disclosure, the ultrasonic diagnostic apparatus includes a fastening part secured to a diagnosis object and a mover moving along the fastening part to obtain consistent quality ultrasound images of the diagnosis object, thereby improving reliability of ultrasonic diagnosis.

In addition, the ultrasonic diagnostic apparatus may reduce user fatigue by allowing automatic movement of the probe, thereby enhancing operability during ultrasonic diagnosis.

In addition, movement of the probe around the diagnosis object is restricted via fabric hook-and-loop fasteners, strings or bands during scanning, instead of a user directly grasping the probe to secure the probe to the diagnosis object, thereby reducing user fatigue.

Further, the ultrasound permeable film may be flexibly bent and the gear rack may also be bent in the same direction as that of the ultrasound permeable film, so that the probe provided to the movable examination part can scan the diagnosis object along the circumference of the object without resistance.

Further, the ultrasonic diagnostic apparatus allows the probe to move on the diagnosis object in the longitudinal direction of the ultrasound permeable film, so that the probe can contact a wide region regardless of the curvature of the diagnosis object, thereby guaranteeing a wide diagnosis area.

Further, the ultrasonic diagnostic apparatus allows scanning of the diagnosis object without direct manual user manipulation and thus provides consistent quality ultrasound images of patients, thereby enhancing reliability of ultrasonic diagnosis.

Further, the ultrasonic diagnostic apparatus is provided with an examination part including the probe, such that the examination part can be brought into close contact with the diagnosis object by expansion of a band member to prevent a gap from being formed between the probe and the diagnosis object during diagnosis, thereby improving the quality of the ultrasound imagery.

Further, the ultrasonic diagnostic apparatus is provided with a gel pad, such that the gel pad can be brought into close contact with the diagnosis object to prevent a gap from being formed between the probe and the diagnosis object during diagnosis, thereby improving the quality of the ultrasound imagery.

Further, the gel pad having a predetermined thickness is disposed between the neck as the diagnosis object and the probe, thereby improving the quality of the ultrasound imagery by eliminating diffuse reflection of ultrasound waves that can occur when the probe is located near the diagnosis object.

Further, although the gel pad needs to be replaced frequently, the gel pad according to the embodiments may be easily attached to or detached from an ultrasound permeable film to facilitate repair and maintenance of the gel pad.

Further, the gel pad is disposed between the probe and a body surface of the diagnosis object, so that a difference in acoustic impedance between the probe and the body surface is gradually reduced to prevent attenuation of acoustic signals, thereby improving the quality of the ultrasound imagery.

Furthermore, the gel pad is disposed between the probe and the diagnosis object, so that a Fresnel Zone created near the probe is distant from the diagnosis object, thereby improving the quality of the ultrasound imagery.

Although some embodiments have been described in the present disclosure with reference to the drawings, it should be understood that these embodiments are given by way of illustration only, and that various modifications, variations, and alterations can be made without departing from the spirit and scope of the present disclosure. Further, although a human thyroid is illustrated as the diagnosis object 10, the ultrasonic diagnostic apparatus according to the embodiments of the present disclosure is obviously applicable to other parts of a person for ultrasonic diagnosis. The scope of the present disclosure should be limited only by the accompanying claims and equivalents thereof.

What is claimed is:

1. An ultrasonic diagnostic apparatus comprising:

a probe configured to transmit an ultrasound signal to a diagnosis object and receive the ultrasound signal reflected therefrom;

a fastening part having a band shape and wound around the diagnosis object; and a mover configured to automatically move the probe along an inner side of the fastening part wound around the diagnosis object, wherein the mover comprises:

a gear rack disposed on the fastening part in a longitudinal direction in which the probe is moved;

a pinion member configured for engaging with the gear rack;

a transport motor configured for driving the pinion member;

a movable plate on which the transport motor, pinion member and probe are mounted; and anti-separation rings each bent at opposite sides of the movable plate and configured to catch lateral sides of the fastening part.

2. The apparatus according to claim 1, wherein the fastening part comprises an ultrasound permeable film connected to the mover and a band member connected to the ultrasound permeable film.

3. The apparatus according to claim 2, wherein the band member comprises a first band member connected to one side of the ultrasound permeable film and a second band member connected to the other side of the ultrasound permeable film.

4. The apparatus according to claim 3, further comprising a fluid supply part connected to the first and second band members to supply hydraulic pressure, the first and second band members configured to expand under the hydraulic pressure.

5. The apparatus according to claim 2, further comprising: a gel pad having a gel therein and disposed on one side of the ultrasound permeable film facing the diagnosis object.

6. The apparatus according to claim 1, wherein the fastening part comprises a resilient gel pad disposed in a moving direction of the mover to surround the mover, and a band member connected to the gel pad.

7. The apparatus according to claim 6, wherein the probe is configured to be moved in a state of contacting an outer surface of the gel pad when probing the diagnosis object.

8. The apparatus according to claim 6, wherein the probe is disposed within the gel pad.

9. The apparatus according to claim 1, wherein the mover comprises:

a drive member configured for supplying rotational power;

a conveyor belt configured to be moved by rotation of the drive member; and a movable mounting part configured to be moved in conjunction with the conveyor belt and having the probe secured to one side thereof.

10. The apparatus according to claim 1, wherein the mover comprises:

a first mover configured for moving the probe in a first direction along the fastening part; and a second mover configured for moving the probe in a second direction different from the first direction along the fastening part.

11. The apparatus according to claim 10, wherein the first mover comprises a first drive member configured for supplying rotational power, a conveyor belt configured to be moved by rotation of the first drive member, and a movable mounting part configured to be moved in conjunction with the conveyor belt and having the probe secured to one side thereof, and wherein the second mover comprises a guide rail formed in the second direction and having first teeth formed on a side surface of the guide rail, a moveable bracket moving along the guide rail, a rotational gear formed on the movable bracket and having second teeth engaging with the first teeth, and a second drive member rotating the rotational gear.

12. The apparatus according to claim 10, wherein the mover further comprises a rotator configured for moving the probe.

13. The apparatus according to claim 12, wherein the rotator comprises:

a rotational motor configured for supplying rotational power;

and a rotational bracket connected to an output shaft of the rotational motor.

* * * * *